United States Patent [19]
Lee

[11] Patent Number: 4,946,380
[45] Date of Patent: Aug. 7, 1990

[54] ARTIFICIAL DEXTEROUS HAND

[75] Inventor: Sukhan Lee, La Canada, Calif.

[73] Assignee: University of Southern California, Los Angeles, Calif.

[21] Appl. No.: 359,086

[22] Filed: May 30, 1989

[51] Int. Cl.$^5$ .............................................. A61F 2/68
[52] U.S. Cl. ...................................... 623/24; 623/21; 623/64; 901/21; 294/111
[58] Field of Search ..................................... 623/21–24, 623/57, 64; 901/21, 38, 39; 294/111, 106

[56] References Cited

U.S. PATENT DOCUMENTS

| | | | |
|---|---|---|---|
| 2,549,074 | 4/1951 | Fishbein et al. ........................ | 623/64 |
| 2,869,139 | 1/1959 | Mosher . | |
| 3,580,099 | 5/1971 | Mosher . | |
| 3,694,021 | 9/1972 | Mullen . | |
| 3,790,002 | 2/1974 | Germond et al. .................. | 901/21 X |
| 3,866,966 | 2/1975 | Skinner, II .......................... | 623/64 X |
| 3,927,424 | 12/1975 | Itoh . | |
| 4,094,016 | 6/1978 | Eroyan . | |
| 4,246,661 | 1/1981 | Pinson . | |
| 4,351,553 | 9/1982 | Rovetta et al. . | |
| 4,364,593 | 12/1982 | Maeda . | |
| 4,367,891 | 1/1983 | Wauer et al. . | |
| 4,685,349 | 8/1987 | Wada et al. . | |
| 4,804,220 | 2/1989 | Rosheim ........................... | 901/21 X |
| 4,865,379 | 9/1989 | Leaver et al. ..................... | 901/39 X |

FOREIGN PATENT DOCUMENTS 488696 2/1976 U.S.S.R. .
2175877A 12/1986 United Kingdom .

OTHER PUBLICATIONS

Los Angeles Times, May 29, 1988, "Odetics to Build a 3-Fingered Robotic Hand for Pentagon Research Agency".

"Studies on a Vertsatile Handling System Having Multijoined Fingers", Tokuji Okada, *Researches of the Electrotechnical Laboratory*, Jul. 1982.

"Design and Construction of a Five-Fingered Robotic Hand", M. Caporali and M. Shahinpoor, *Robotics Age*, Feb. 1984.

*Primary Examiner*—Richard J. Apley
*Assistant Examiner*—Joe H. Cheng
*Attorney, Agent, or Firm*—Pretty, Schroeder, Brueggemann & Clark

[57] ABSTRACT

An artificial dexterous hand is provided for conformally engaging and manipulating objects. The hand includes an articulated digit which is connected to an engagement sub-assembly and has a first shape adaption mechanism associated with it. The digit has a digit base and first and second phalanges. The digit base is operatively interconnected to the first phalange by a base joint having a base pulley. The phalanges are operatively interconnected by a separate first phalange joint having a first phalange pulley. The engagement sub-assembly includes a tendon, which is received by the base pulley and by the first phalange pulley, and an actuation device for selectively tensioning the tendon. The first shape adaption mechanism is responsive to and receives the tendon. It is also situated between the base joint and the first phalange joint and is connected to the first phalange. Upon actuation by the actuation device, the phalanges are caused to pivot relative to the base joint and the second phalange is caused to pivot relative to the first phalange. At the same time, the first shape adaption mechanism controls the sequence of the aforementioned pivoting of the phalanges through application of braking force to the tendon.

26 Claims, 8 Drawing Sheets

FIG. 3A
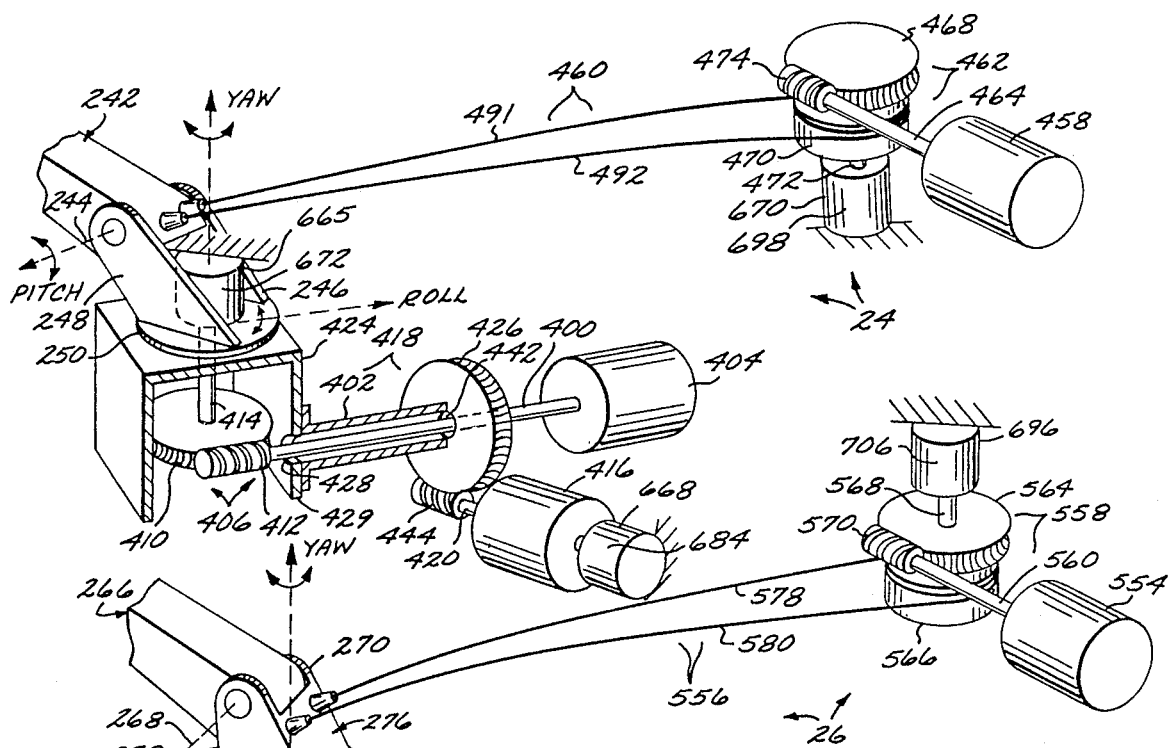
FIG. 3B
FIG. 3C
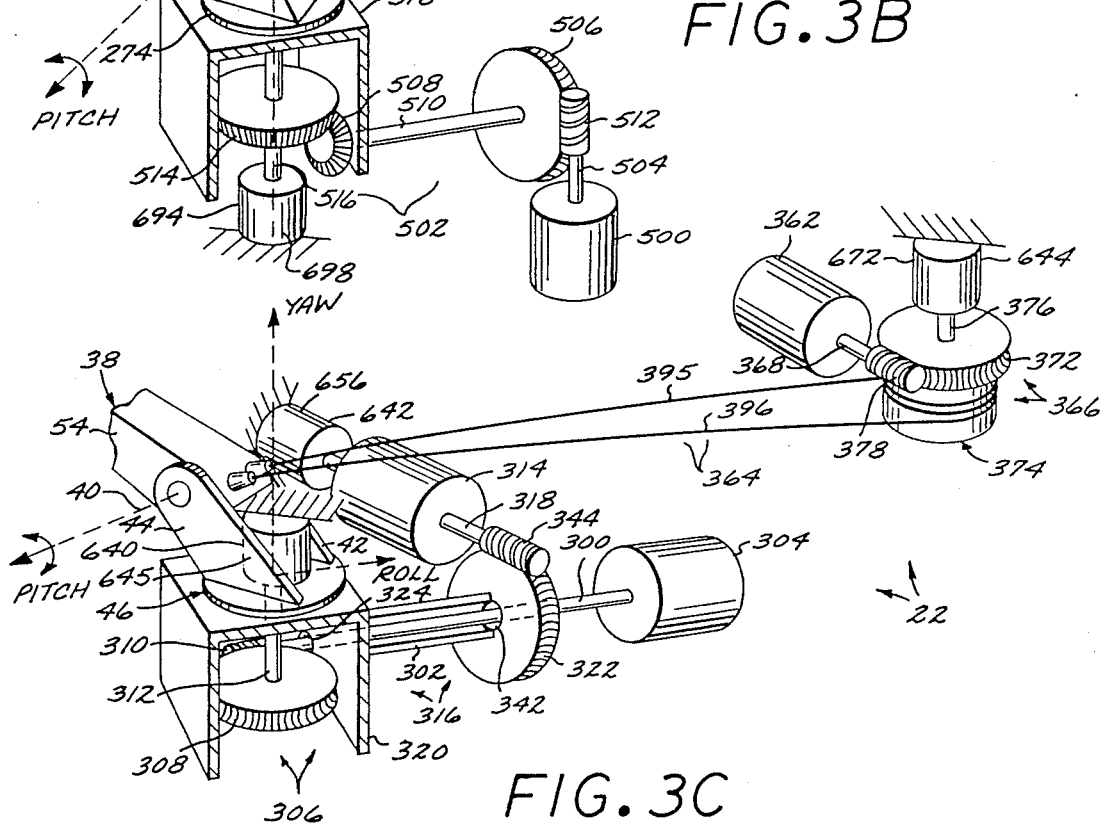

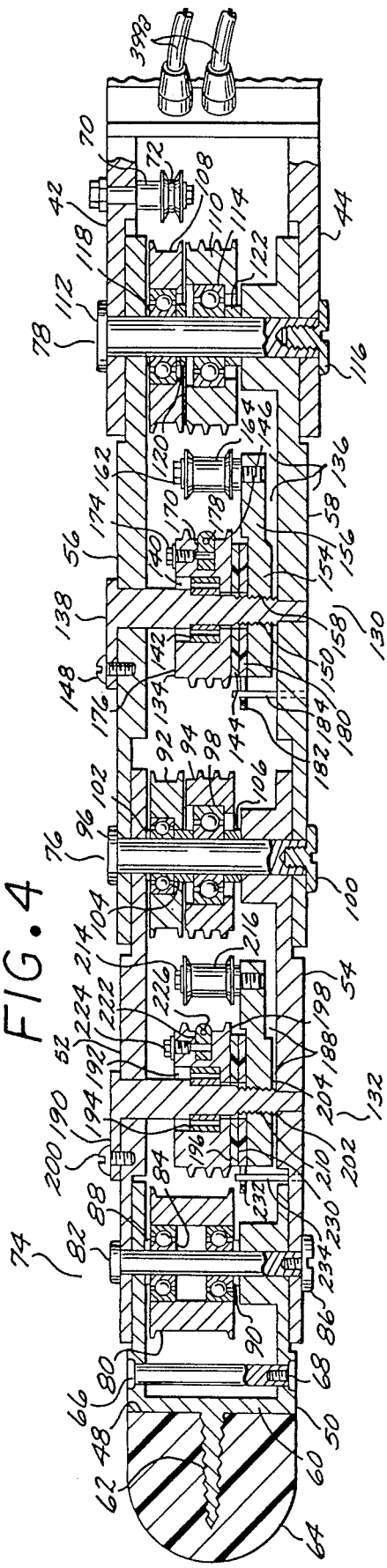

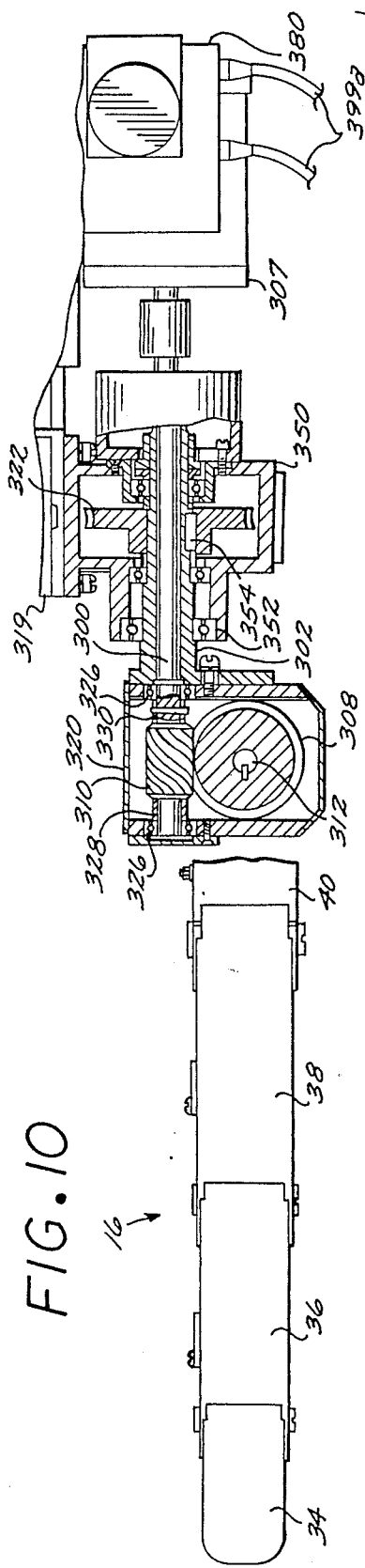

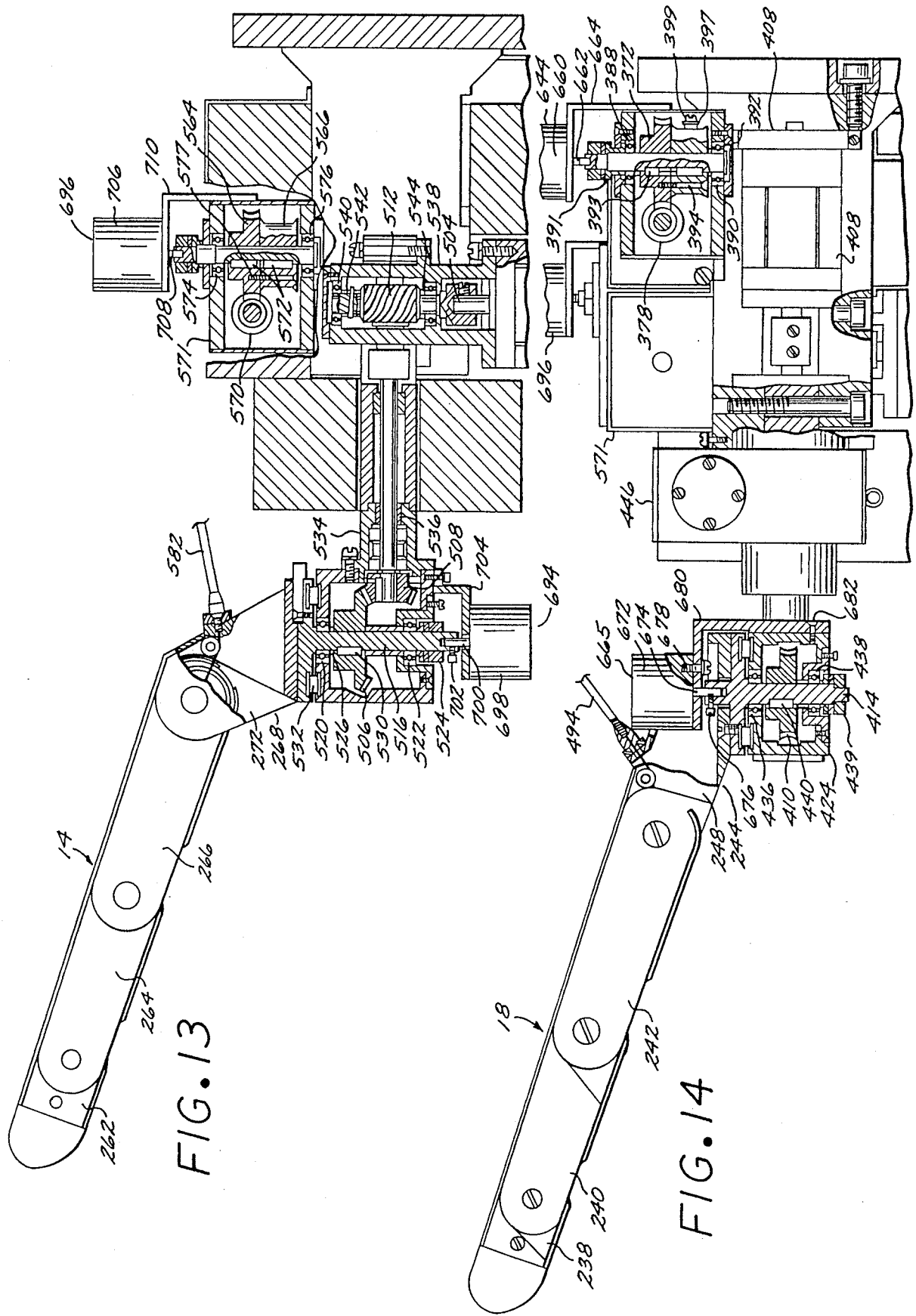

ARTIFICIAL DEXTEROUS HAND

This invention was made with government support under contract no. 956501 awarded by the California Institute of Technology, Jet Propulsion Laboratory to the University of Sourthern California. This contract is a subcontract under NASA contract NAS7-918. The United States Government has certain rights in the invention.

BACKGROUND OF THE INVENTION

This invention relates generally to artificial hands and, more particularly, to an artificial dexterous hand having one or more articulated digits that can be versatilely configured so as to more easily adapt to differently shaped objects.

A variety of artificial hands are known and have widespread applications in many diverse fields, such as prosthetics, space or undersea exploration and the like. Industrial applications for artificial hands also abound. The existence of these and other applications has created an increasing need for artificial hands to reliably perform many complex or delicate tasks, particularly in certain work environments that may be innately unsuitable for task completion with the aid of an artificial hand. This need has in turn give rise to an accompanying need for artificial hands which are capable of assuming more configurations and more versatilely adapting to various work environments and to various shapes of objects.

For the purpose of allowing artificial hands to assume various configurations, artificial hands typically have articulated digits. Each digit commonly has a number of phalanges which are usually separate mechanical linkages. Each successive two phalanges are in turn interconnected by one of a series of joints which permit the phalanges to pivot or pitch relative to each other. Some joints have a series of gears for accomplishing relative pivoting or pitching of two successive phalanges. Still other joints may have pulleys which are each interconnected by a tendon or wire that is received by each pulley. In this case, the application of tensile force to the tendon causes each pulley to rotate and, thereby, pivot or pitch the phalanges relative to each other.

These known construction of joints, tend, however, to have fundamental disadvantages. A gear construction for the joints may result in an unduly heavy digit which can require a rather expensive assemblage of actuation mechanisms for operation of the hand. A gear construction can also create an artificial hand which is overly rigid or jaw-like in its movements. On the other hand, the aforementioned pulley and tendon construction may result in a digit which is too flexible and tends to easily become unstable. Moreover, both types of constructions tend to cause the phalanges of the digit to pivot arbitrarily, unless their pivoting is controlled by a complex and costly assemblage of actuation and control mechanisms associated with each joint.

Further, the digits of certain existing hands tend to be unstable during pivoting and to inadequately compensate for the effects of forces that develop near the outer or fingertip joint during the grasping or manipulation of an object by the hand. That is, the outer joints of a digit tends to experience greater forces than the other joints of the digit. These forces tends to undesirably propagate from the outer joint to the other joints such that the finger becomes unstable and may be unable to retain its desired configuration. Some efforts to address this problem employ separate motors to attempt to control the pivoting at each joint. This is, however, costly and requires a cumbersome assemblage of actuation mechanisms and complex control systems.

The nature of certain tasks and the inherent characteristics of certain work environments also require the digits of the hand to perform complex or delicate tasks without undue delay. Existing digits tend to be unable to suitably conform their pivoting or pitching configurations in a relatively short period of time. Moreover, existing digits also tend to be unable to versatilely alternate between robust and delicate modes of grasping and manipulation without expensive control mechanisms.

It should, therefore, be appreciated that there has existed a definite need for an artificial dexterous hand having one or more digits that are better capable of versatilely adapting their respective configurations to conform to various shapes of objects and which are constructed in a manner more conducive to digit stability and efficient control of the sequence of pivoting of the phalanges corresponding to each digit.

SUMMARY OF THE INVENTION

The present invention, which addresses the aforementioned need, is embodied in an artificial hand which can versatilely adapt its configuration to differently shaped objects and which is more stable during operation. The hand includes an articulated digit which is operatively connected to an engagement sub-assembly and has a first shape adaption mechanism associated with it. The digit has a digit base and first and second phalanges. The digit base is operatively interconnected to the first phalange by a base joint having a base pulley. The first and second phalanges are operatively interconnected by a separate first phalange joint having a first phalange pulley. The engagement sub-assembly includes a tendon, which is received by the base pulley and by the first phalange pulley, and an actuation device for selectively tensioning the tendon.

The first shape adaption mechanism is responsive to and receives the tendon. It is also situated between the base joint and the first phalange joint and is connected to the first phalange. When the actuation device increasingly tensions the tendon, the resulting tensile force propagates the base joint and to the first shape adaption mechanism. At the same time, the first shape adaption mechanism selectively applies increasing braking force to the tendon. This force restrains the second phalange from pivoting relative to the first phalange by impeding the propagation of sufficient tensile force to the first phalange joint. At the same time, the first shape adaption mechanism permits the first and second phalanges to pivot together relative to the base joint. The first shape adaption mechanisms also selectively permits the aforementioned relative pivoting of the first and second phalanges when the tensile force has exceeded the maximum sustainable braking force. The shape adaption mechanism thus selectively controls the sequence of the pivoting of the phalanges and ensures that the digit and its constituent phalanges retain their stability during operation and, particularly, during pivoting.

The digit can also have three or more interconnected phalanges. In that event, there is a corresponding increase in phalange joints and an additional shape adaption mechanism is advantageously located between each successive pair of phalange joints. Each additional shape adaption mechanism then functions similarly to the first shape adaption mechanism.

In one preferred form of the invention, the first shape adaption mechanism includes a first brake pulley and a first brake which are each operatively disposed around a first brake rod. The first brake pulley is received by the tendon and has a first friction pad secured to its interradial surface, while the first brake rod has a series of first external threads which can define a triple threaded screw type thread pattern. The first brake is engageable with the first external threads and is contactable with the first brake pulley. It selectively regulates the movement of the first brake pulley by applying increasing braking force to the first brake pulley in response to increased tension exerted by the tendon on the first brake pulley.

In more detailed aspects of the aforementioned preferred form of the invention, the first brake includes a first brake disc which is disposed around the first brake rod and which is engageable with the first external threads. The first brake disc also has a first brake arm which has a first arm roller connected to it. The first arm roller receives the tendon which in turn exerts force on the first arm roller when the tendon is tensioned. A suitable biasing element is also secured to the first brake arm and to the first phalange in order to provide the first brake disc with a threshold braking force against the first brake pulley. Additionally, the first brake has a suitable mechanism, which is connected to the first brake pulley, for securing the tendons in the first brake pulley.

In still more detailed aspects of the aforementioned preferred form of the invention, the first brake includes a first secondary brake rod, which is connected to the first phalange, and a first friction plate that is slidably connected to the first secondary rod. The first friction plate is also disposed between the first brake disc and the first brake pulley and is movable along with the first brake rod in response to actuation from the first brake disc.

In accordance with an alternative form of the invention, the first shape adaption mechanism is similar to the aforementioned preferred form, except that the friction plate and first secondary rod are replaced with a substantially dish-shaped washer. The dish-shaped washer is disposed around the first brake rod and is located between the first brake pulley and the first brake disc. It is further movable along with the first brake rod in response to actuation from the first brake disc.

In a further alternative form of the invention, the first shape adaption mechanism includes a first brake pulley which is operatively disposed around a first brake rod and which is engageable with a first brake. The first brake pulley is received by the tendon, while the first brake rod is connected to the first phalange. The first brake is contactable with the first brake pulley and selectively regulates the movement of the first brake pulley through application of increasing braking force to the first brake pulley in response to increasing tension exerted by the tendon on the first brake pulley.

The first brake of the immediately aforementioned alternative form includes a first brake arm which is pivotally secured to a secondary brake rod near one end of the secondary brake rod and on the other end has a first arm rod connected to it. The secondary brake rod is secured to the first phalange, while the first arm rod receives the tendon. Moreover, the first brake includes a first brake member that cooperates with a first biasing element for the purpose of applying both threshold and increasing braking force to the first brake pulley. The first brake member has a concave outer surface which is engageable with the outer surface of the first brake pulley and is secured to the first brake arm. The first biasing element is secured to one end of the first brake arm and on its other end to the first phalange.

In applications where more than one shape adaption mechanism is employed in the digit, each additional mechanism would be constructed similarly to the particular form of the invention that is used for its companion first shape adaption mechanism. Each additional mechanism would, however, preferably be secured to a separate successive phalange. Thus, in the case of two shape adaption mechanisms, the first mechanism would be secured to the first phalange and the second mechanism would be secured to the second phalange.

Other features and advantages of the present invention will become more apparent from the following detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 3 is a simplified and somewhat enlarged perspective view of the engagement assembly of the artificial dexterous hand of the present invention.

FIG. 4 is an enlarged transverse sectional view of the left thumb of the hand, taken substantially along lines 4—4 of FIG. 2, and illustrating one preferred embodiment of the shape adaption mechanism of the present invention.

FIG. 5 is an enlarged schematic representation of the interior of the left thumb illustrated in FIG. 4.

FIG. 10 is an enlarged, fragmentary top view of the left thumb and portions of the left thumb and right thumb and finger engagement sub-assembly with selected features illustrated by way of cut-away views.

FIG. 11 is an enlarged fragmentary, side elevational view of the left thumb and portions of the left thumb engagement sub-assemblies with certain features illustrated by way of cut-away views.

FIG. 12 is an enlarged, fragmentary bottom view of a portion of the right thumb engagement sub-assembly with selected features illustrated by way of cut-away views FIG. 13 is an enlarged fragmentary, side elevational view of the finger and portions of the finger engagement sub-assembly with selected features illustrated by way of cut-away views.

FIG. 14 is an enlarged fragmentary, side elevational view of the right thumb and selected portions of the left thumb, right thumb and finger engagement assemblies with selected features illustrated by way of cut-away views.

DESCRIPTION OF THE PREFERRED EMBODIMENTS

Figure 1:
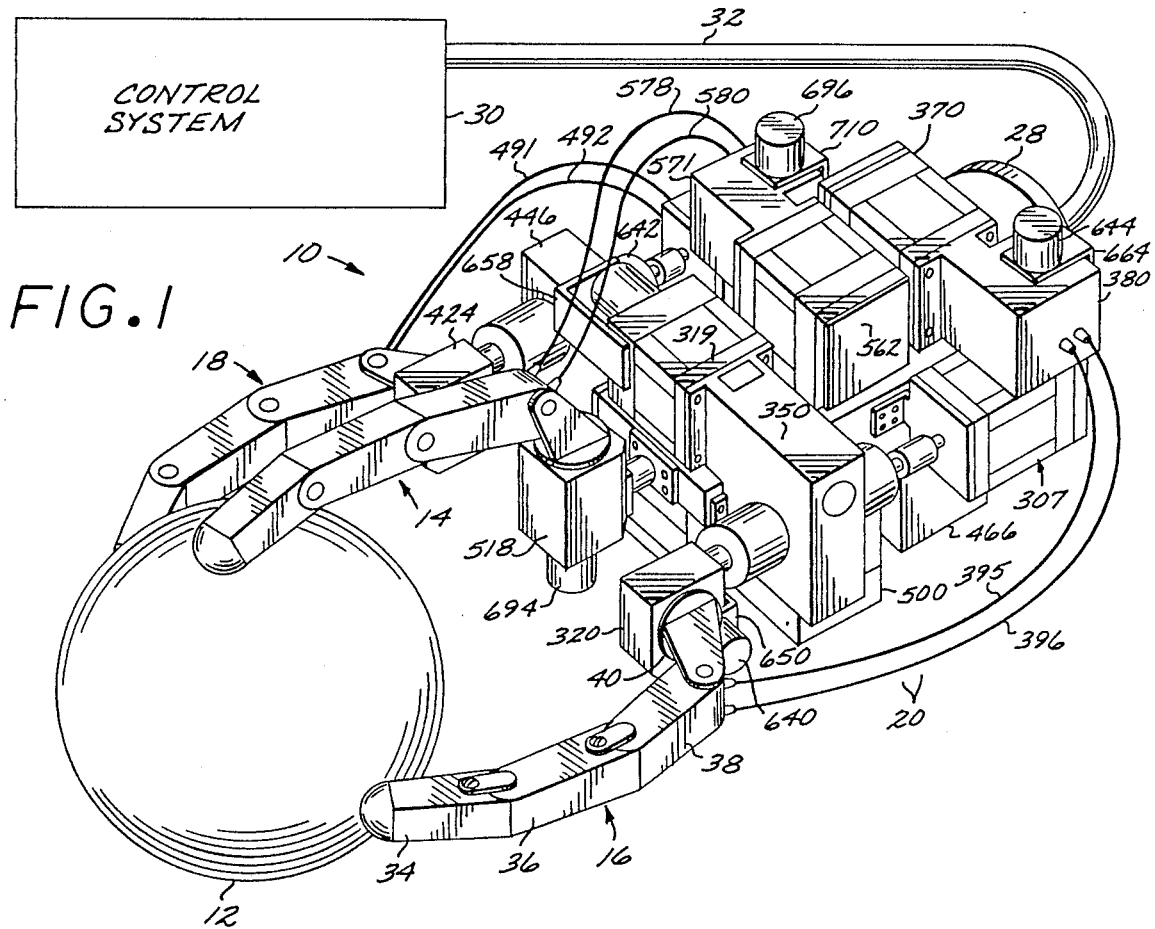
FIG. 1 is a perspective view of the artificial dexterous hand of the present invention associated with an accompanying control system and shown grasping a sphere.

With reference now to the drawings, and particularly to FIG. 1, there is shown an artificial dexterous hand 10 for grasping and manipulating objects, such as a sphere 12, in accordance with the present invention. The hand 10 includes a center finger or finger digit 14, which is interposed between left and right thumbs or thumb digits 16 and 18, and a hand engagement assembly 20 that is operatively connected to the finger or finger digit 14 and thumbs or thumb digits 16 and 18. The engagement assembly 20 contains left and right thumb engagement subassemblies 22 and 24 and a finger engagement sub-assembly 26 which are clustered together so as to economize on space and allow the hand 10 to operate in more confined environments. (See FIGS. 1-2, 15.) The engagement assembly 20 is also secured to a suitable support structure 28 and connected to an appropriate control system 30. (See FIGS. 1 and 15.) The support structure 28 lends stability to the engagement assembly 20 and to the finger 14 and thumbs 16 and 18 during operation of the hand 10. The control system 30 is linked to the engagement assembly 20 by a control cable 32 that contains suitable wiring and is received by an aperture 33 in the support structure 28. The control system 30 permits selective and sensitive regulation of the respective movements of the finger 14 and thumbs 16 and 18.

The present invention provides an artificial dexterous hand 10 having articulated digits that can be versatilely configured so as to more easily adapt to differently shaped objects in many different work environments. The digits of the hand 10 are each constructed in a manner that tends to make each digit more stable during operation and permits efficient and effective control of the pivoting of each digit along its associated articulated areas. The hand 10, therefore, tends to have a significant degree of kinesthetic perception and to more properly perform tasks that may require it to alternate between robust and delicate modes of grasping and manipulation. The aforementioned features also tend to diminish the complexity, cost and size of the hand 10 and particularly, to reduce the complexity of the engagement assembly that would otherwise be necessary. At the same time, the lesser degree of complexity, and the decreased size and cost do not tend to adversely affect the overall functional capability of the hand 10.

Figure 2:
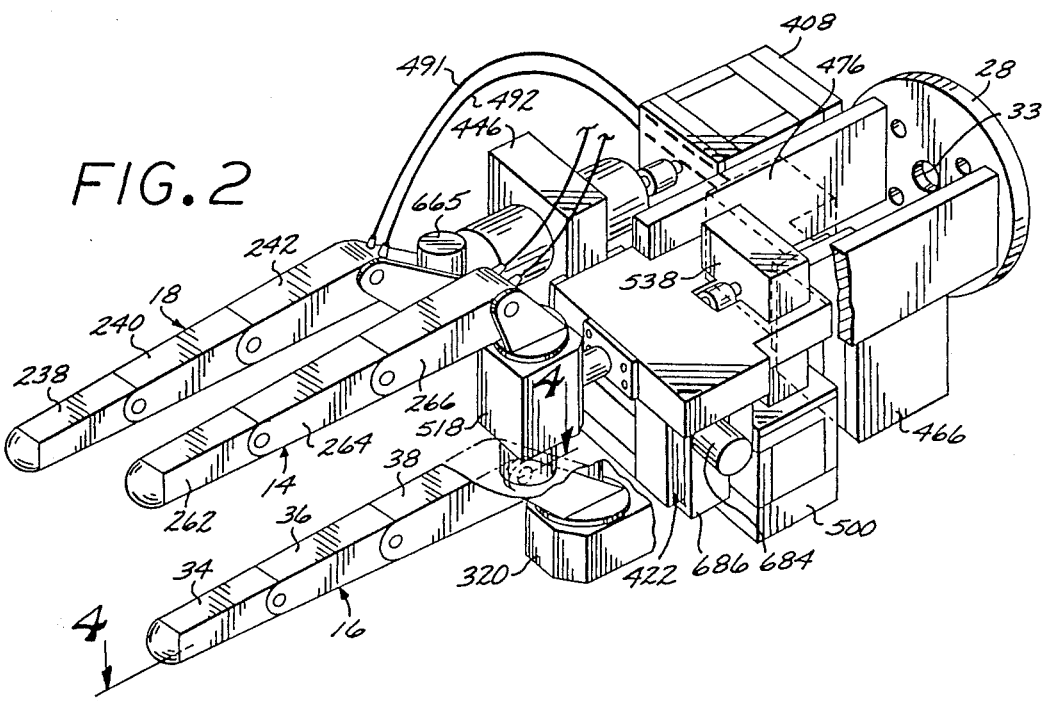
FIG. 2 is a fragmentary perspective view of the artificial dexterous hand of FIG. 1 illustrating the respective configurations of the digits of the hand in their respective fully extended or rest positions and further illustrating the center finger and right thumb engagement sub-assemblies.

In accordance with one preferred form of the invention, the finger 14, thumbs 16 and 18 and the engagement assembly 20 are constructed in a manner that permits the hand 10 to be configured substantially like a human left hand, a human right hand, an integrated form of a human left hand and a human right hand, or three fingers of a human hand. Thus, substantially like their human counterparts, the finger 14 and thumbs 16 and 18 have multiple degrees of freedom and the capability to assume a wide variety of configurations in three dimensional space. As shown in FIGS. 1-2 the left and right thumbs 16 and 18 and finger 14 are operatively connected respectively to the left thumb sub-assembly 22, right thumb sub-assembly 24 and finger sub-assembly 26. Each sub-assembly 22, 24 and 26, therefore, selectively moves its corresponding digit in response to selective commands from the control system 30.

More particularly, with reference first to the left thumb 16 and the left thumb engagement sub-assembly 22, the left thumb 16 includes outer, middle and inner left thumb phalanges or linkages 34, 36 and 38 respectively which together are coupled to a left thumb base or base linkage 40. (See FIGS. 1-3.) The left base linkage 40 occupies a position somewhat similar to that occupied by a metacarpal of a human hand. It includes an oppositely disposed pair of somewhat knuckle shaped left links 42 and 44 that are securely seated on a left base plate 46 that has a substantially circular cross-section.

As more fully described below, the left base linkage 40 is connected to the left thumb engagement subassembly 22 so as to permit the left thumb 16 to yaw, roll and pitch or pivot relative to three separate left thumb base axes running through the left thumb base 40. With reference to FIG. 3(c), it will be observed that the axis passing vertically through the left thumb base 40 corresponds to the axis relative to which the left thumb 16 yaws (hereinafter, "left thumb base yaw axis".) The axis passing horizontally through the left thumb base 40 is associated with rolling of the left thumb 16 (hereinafter, "left thumb base roll axis".) The remaining axis, which is substantially orthogonal to the transverse axis of the left thumb 16 in its fully extended position, is associated with pitching or pivoting of the left thumb 16. It preferably moves along with the left thumb 16 when it yaws (hereinafter, "left thumb pitch or pivoting base axis".) The aforementioned left thumb base axes are advantageously, but not necessarily, substantially mutually orthogonal to each other. Thus, when the position of the left thumb 16 corresponds to the fully extended or rest position of the left right thumb 16 shown in FIG. 2, the left thumb base axes will be mutually orthogonal. On the other hand, where the left thumb 16 has yawed into the position shown in FIG. 3(c) and, thereby, carried the left thumb base pitch axis through a similar yaw angle, the left thumb base roll and pitch axes will no longer be mutually orthogonal.

Each of the left thumb phalanges 34, 36 and 38 is hollow and bears some resemblance in size and shape to its counterpart portion of a human middle finger as the middle finger would appear to an observer. As such, they together define a left thumb 16 that is rather similar in dimensions to a human middle finger. As depicted in FIG. 4, the outer left phalange 34 has opposing upper and lower side linkages 48 and 50. Correspondingly, the middle left phalange 36 has opposing upper and lower side linkages 52 and 54, while the inner left phalange has opposing upper and lower side linkages 56 and 58. The upper and lower linkages 48 and 50 are each necked down such that they are overlapped respectively by the opposing upper and lower side linkages 52 and 54 of the middle left phalange 36. So too with the opposing side linkages 52 and 54 of the middle left phalange 36 relative to opposing side linkages 56 and 58 of the inner left phalange 38 and with opposing side linkages 56 and 58 of the inner left phalange 38 relative to the left links 42 and 44 of the and left thumb base or base linkage 40.

The outer left phalange 34 can also have top cross-member 60 which is formed integral with the sections of the upper and lower side linkages 48 and 50 that are located farthest from the upper and lower side linkages 52 and 54 respectively. The top member 60 is oriented substantially orthogonal to the transverse axis of the left thumb 16 and has an integrally formed cap screw 62 that protrudes transversely toward the tip of the left thumb 16. (See FIG. 4.) The cap screw 62 can then receive a somewhat domeshaped cap 64 that makes the left thumb 16 appear more anthropomorphic and has a contour that may facilitate grasping and manipulation of objects.

The outer left phalange 34 further advantageously has a left tendon pin 66 that extends axially through the outer left phalange 34 and is secured to the upper and lower side linkages 48 and 50. It is also located adjacent the top member 60 and is substantially orthogonal to it. The left pin 66 can be better retained within the outer left phalange 34 by a suitable left pin screw 68. The screw 68 is threaded into a bore in the left pin 66 and has its end oriented substantially flush with the lower linkage 50. The left link 42 of the left base linkage 40 can also securely receive a left link pin 70 around which a left link pulley 72 is disposed. The significance of the left tendon pin 66 and left link pulley 72 will become apparent during later discussion of the pitching or pivoting of the left thumb 16. The left phalanges 34, 36 and 38 can also be surrounded by a suitable cover to protect them from the environment.

For the purpose of furnishing the left thumb 16 with articulated characteristics of a human finger, the interior of the left thumb 16 has separate outer, middle, and inner or base left thumb joints 74, 76 and 78. The outer left joint 74 is essentially interposed between the upper side linkages 48 and 52 and lower side linkages 50 and 54. Correspondingly, the middle left joint is essentially interposed between the upper side linkages 52 and 56 and the lower side linkages 54 and 58. Finally, the inner or base left joint is essentially interposed between the upper side linkage 56, the left link 42, and the lower side linkage 58 and the left link 44. The outer left joint 74 operatively attaches the outer left phalange 34 to the middle left phalange 36, while the middle left joint 76 operatively attaches the middle left phalange 36 to the inner left phalange 38. Correspondingly, the inner left joint 78 operatively attaches the inner left phalange 38 and the left thumb base or base linkage 40 to each other.

As depicted in FIG. 4, the outer left joint 74 has an outer left pulley 80 that defines a central aperture for receiving an outer left thumb rod 82. Suitable outer left bearings 84 are situated within the aperture for allowing the outer left pulley to more stably rotate relative to the outer left rod 82. The outer left rod 82 extends axially through the side linkages 52 and 54 of the middle left phalange 36. It also defines a bore for receiving a suitable outer left rod screw 86 that assists in retaining the outer left rod 82. The head of the screw 86 abuts the side linkage 54 of the middle left phalange 36.

For the purpose of more snugly retaining the outer left bearing 84 and stabilizing the outer left pulley 80, the outer left joint 74 can also have a pair of outer left sleeves 88 and 90. The sleeve 88 is disposed between the pulley 80 and the side linkage 48 of the outer left phalange 34, while the sleeve 90 is disposed between the pulley 80 and the side linkage 50 of the outer left phalange 34.

The middle and inner left joints 76 and 78 are of similar construction, except for some differences in the individual sizes of the joint components that may be needed to compensate for the differing pitching or pivoting loads experienced by the left phalanges 34, 36 and 38 and the overall dynamics of the left thumb 16. The middle left joint 76 preferably, but not necessarily, has a substantially contiguous pair of middle left pulleys 92 and 94 that define a central aperture for receiving a middle left thumb rod 96. Suitable middle left bearings 98 are situated within the aperture for allowing the middle left pulleys 92 and 94 to more stably rotate relative to the middle left rod 96. The middle left rod 96 extends axially through the side linkages 56 and 58 of the inner left phalange 38. It also defines a bore for receiving a suitable middle left rod screw 100 that assists in retaining the middle left rod 96. The head of the screw 100 abuts the side linkage 58 of the inner left phalange 38.

A middle washer 102 can be disposed about the middle left rod 96 and adjacent to the side linkage 52 of the middle left phalange 36 in order to prevent undue axial movement of the middle left pulleys 92 and 94. The snugness of the fit of the bearings 98 and the stability of the middle left pulleys 92 and 94 can also be augmented by disposing a pair of middle sleeves 104 and 106 about the middle left rod 96. When so disposed, the sleeve 104 is located between each of the middle left pulleys 92 and 94 and the sleeve 106 is located adjacent the side linkage 54 of the middle left phalange 36.

In like manner, the inner left joint 78 preferably, but not necessarily, has a substantially contiguous pair of inner left pulleys 108 and 110 that define a central aperture for receiving an inner left thumb rod 112. Suitable inner left bearings 114 are situated within the aperture for allowing the inner left pulleys 108 and 110 to more stably rotate relative to the inner left rod 112. The inner left rod 112 extends axially through the left links 42 and 44. It also defines a bore for receiving a suitable inner left rod screw 116 that assists in retaining the rod 112 within the links 42 and 44 of the left thumb base 40. The head of the screw 116 abuts the link 44.

Similar to the middle left joint 76, the inner left joint 78 can also have a inner washer 118 and a pair of inner sleeves 120 and 122. The inner washer 118 is situated adjacent the upper side linkage 56 and disposed around the inner left rod 112. The sleeves 120 and 122 are disposed around the inner left rod 112. The sleeve 120 is located between each of the inner left pulleys 108 and 110, while sleeve 122 is located adjacent the lower side linkage 58. It will be appreciated that the outer, middle, and inner left thumb joints 74, 76 and 78 can be constructed in a number of other ways that achieve relative pivoting of the left thumb phalanges 34, 36 and 38. Thus, for instance, a single pulley could be used for each joint.

In accordance with a separate feature of the invention, the interior of the left thumb 16 can also be provided with inner and outer shape adaption mechanisms 130 and 132. The mechanisms 130 and 132 together control the sequence of pitching or pivoting of the left phalanges 34, 36 and 38 relative to each other and of the left phalanges 34, 36 and 38 relative to the left thumb base or base linkage 40. They also allow the left thumb 16 to more versatilely configure itself to conform to different shapes of objects More particularly, as shown in FIG. 4, the inner shape adaption mechanism 130 is situated between the middle and inner or base left thumb joints 76 and 78. It includes an inner left brake pulley 134 and an inner left brake 136 which are each disposed around an inner left brake rod 138. (See FIGS. 4–5.)

The inner brake pulley 134 is selectively rotatable in both a clockwise and counterclockwise direction relative to the inner brake rod 138. It has a centrally located inner bore 140 which receives needle or other suitable bearings 142. The bearings 142 are abutable with the inner brake rod 138. They, therefore, tend to reduce frictional forces between the inner brake rod 138 and the inner brake pulley 134 and to facilitate proper rotation of the pulley 134. The inner brake pulley 134 can also have a suitable friction pad 144 affixed to its inner radial surface 146. The pad 144 faces the inner left brake 136. As will become evident below, the pad 144 reduces wear on the inner brake pulley 134 during operation of the inner shape adaption mechanism 130.

The inner left brake rod 138 extends axially through the interior of the left thumb 16 and is received through bores (not shown) in the opposing side linkages 56 and 58 of the inner left phalange 38. It is also secured to the side linkage 56 of the inner left phalange 38 by an appropriate set screw 148. The inner brake rod 138 further becomes tapered as it extends from the side linkage 56 to the side linkage 58 of the inner left phalange 38 and has a series of external inner rod threads 150. The threads 150 define a thread pattern that is substantially similar to the thread pattern that is characteristic of a triple threaded screw. The threads 150 advantageously, but not necessarily, begin adjacent to the inner radial surface 146 of the inner brake pulley 134 and terminate adjacent to the side linkage 58 of the inner left phalange 38.

As depicted in FIGS. 4–5, the inner left brake 136 includes an inner left brake disc 152. The disc 152 has a substantially circular body 154 formed integral with an inner left brake arm 156. It thus somewhat resembles a common frying pan.

The inner brake disc 152 is disposed around the portion of the inner brake rod 138 which has the inner rod threads 150. It defines a centrally located bore which has a series of internal brake threads 158 that can mate with and thereby, engage the inner rod threads 150. The brake threads 158, therefore, too define a thread pattern that is substantially similar to the thread pattern characteristic of a triple threaded screw. However, as evident from FIG. 4, the length of the thread pattern formed by the brake threads 158 is smaller than the length of the thread pattern formed by the inner rod threads 150. Therefore, similarly to a nut located on a threaded bolt, the inner brake disc 152 can be threaded along the inner brake rod 138 and into engagement with the inner radial surface 146 of the inner brake pulley 134. It thus provides a braking force which can restrain rotation of the inner brake pulley 134.

The top portion 160 of the inner brake arm 156 defines an axial opening for securely receiving an inner arm rod 162 that has an inner arm roller 164 preferably securely disposed around it. When the inner arm rod 162 is received in this manner, the common transverse axis of the rod 162 and inner arm roller 164 is oriented substantially parallel to the transverse axis of the inner left brake rod 138. Moreover, the inner arm roller 164 has substantially the same in width as the width of the inner brake pulley 134.

For the purpose of more selectively and effectively regulating the braking force exerted by the left brake disc 152, the inner left brake 136 also advantageously includes a pair of oppositely disposed inner left biasing elements 166 and 168, which can be suitable helical springs. The biasing element 166 has one of its ends secured to the top portion 160 of the inner brake arm 156 and its other end secured to the side linkage 58 of the inner left phalange 38. The biasing element 168 has one of its ends secured to the top portion 160 of the inner brake arm 156, while its other end is secured to the side linkage 56 of the inner left phalange 38.

As shown in FIG. 5, the equilibrium or rest position of the inner left brake 136 corresponds to the position in which the left thumb 16 is fully extended. In this equilibrium position, therefore, the biasing element 166 exerts a threshold initial spring force on the inner brake arm 156. This tensile or pulling force maintains the inner brake disc 152 in its equilibrium state of engagement with the inner rod threads 150. This in turn provides the inner brake disc 152 with a threshold braking force that is initially exerted on the inner radial surface 146 of the inner brake pulley 134. The inner brake pulley 134, therefore, is restrained from rotating clockwise relative to the inner brake rod 138.

As will become more evident from later discussion, the inner brake disc 152 will not further engage the inner rod threads 150, and thereby will not move further inward against the inner radial surface 146 of the pulley 134, until any force incident on the inner arm roller 164 is sufficient to move the inner brake arm 156 downward. This force will also have to overcome the threshold restoring force of the biasing element 168. In the event that there is sufficient force, the inner brake arm 156 will move downward and the inner brake disc 152 will further engage the inner rod threads 150. Thus, the braking force against the inner brake pulley 134 will augment and, thereby, further resist rotation of the inner brake pulley 134. The braking force will tend to be greatest whenever the force incident on the inner arm roller 164 has caused the biasing element 166 to become substantially fully compressed or when the inner brake disc 152 simply cannot move further inward.

It will be understood that a triple threaded screw pattern is particularly advantageous here, since it facilitates speedy movement of the inner brake disc 152 in either direction along the inner brake rod 138. The inner brake pulley 134 and the inner brake disc 152, therefore, tend not to remain undesirably locked together after braking the force has subsided The inner left brake 136 thus tends to more easily reassume its equilibrium position.

It will be appreciated that it is desirable that the inner left brake 136 continually be able to reassume its return equilibrium position shown in FIG. 5. Generally, the inner brake 136 will tend to do so when any force incident on the inner arm roller 164 subsides such that there is decrease in the braking force exerted by the inner brake disc 152. At this point, the restoring force of the biasing element 166 in its compressed condition will tend to help overcome the subsiding force incident on the inner arm roller 164 and urge the inner arm rod 162 upward. In some cases, however, remnant frictional forces that may exist between the inner brake pulley 134 and the inner brake disc 152 may counteract the restoring force of the biasing element 166 and, therefore, tend to prevent the inner left brake 136 from returning to equilibrium. In that event, the biasing element 168 serves to provide an additional force which counteracts the remnant frictional forces and assists the inner left brake 136 in reassuming its equilibrium position.

The inner left brake 136 is also associated with a somewhat semi-ovular, but substantially flat, inner tendon brake pin 170. It is situated within a radial bore within the inner brake pulley 134 and protrudes outwardly from the outer surface 172 of the inner brake pulley 134. It is also secured to the pulley 134 by a suitable screw pin 174 that fits within an axial bore in the pulley 134 and has a screw head which is substantially flush with the outer radial surface 176 of the inner brake pulley 134.

The tendon brake pin 170 defines an inner tendon cavity 178 which is situated adjacent the outer surface 172 of the inner brake pulley 134. The pin 170 also has its transverse axis oriented substantially perpendicular to the transverse axis of the screw pin 174. The functions of the screw pin 174 and tendon pin 170 will become evident during later discussion of the pitching or pivoting of the left thumb 16.

In order to prevent the inner left brake disc 152 from undesirably locking with the inner brake pulley 134, the inner left brake 136 can also include a suitable inner left friction plate 180 which is disposed around the inner brake rod 138. The plate 180 is interposed between the inner brake disc 152 and the friction pad 144 associated with the inner brake pulley 134 such that it is substantially contiguous with the friction pad 144 and the inner brake disc 152. (See FIG. 4.) It also has a hollow inner friction stem 182 which protrudes transversely toward the middle left joint 76 and is slidably connected to a slender secondary brake pin 184. The secondary brake pin 184 is connected to the side linkage 58 of the inner left phalange 38. Consequently, the inner friction plate 180 will tend to only translate, rather than also rotate, along the inner brake rod 138. The absence of any significant rotation will make the friction plate 180, and thus the inner brake disc 152, less conducive to locking with the inner brake pulley 134. Thus, when the application of braking force is not desired, the inner brake pulley 134 can function more independently of the inner brake 136.

It will be appreciated that the particular types of biasing elements 166 and 168 and other components of the inner shape adaption mechanism 130 chosen will substantially depend upon the dynamics of the left thumb 16 and the particular tasks to be accomplished. As will become evident below, however, the biasing elements 166 and 168 preferably have the requisite force characteristics to permit the desired controlled, sequential pitching or pivoting of the left phalanges 34, 36 and 38 relative to each other and of the left phalanges 34, 36, and 38 relative to the left thumb base or base linkage 40.

The outer shape adaption mechanism 132 is constructed essentially similar to, and functions essentially alike, the inner shape adaption mechanism 130. More particularly, as depicted in FIGS. 4–5, the outer shape adaption mechanism 132 is situated between the outer and middle left thumb joints 74 and 76. It includes an outer left brake pulley 186 and an outer left brake 186 which are each disposed around an outer left brake rod 190.

The outer brake pulley 186 is selectively rotatable relative to the outer brake rod 190 and has a centrally located inner bore 192 which receives needle or other suitable bearings 194. The bearings 194 are abutable with the outer brake rod 190. They, therefore, tend to reduce frictional forces between the outer brake rod 190 and the outer brake pulley 186 and to facilitate proper rotation of the pulley 186. The outer brake pulley 186 can also have a suitable friction pad 196 affixed to its inner radial surface 198 for reducing wear on the pulley 186.

The outer left brake rod 190 extends axially through the interior of the left thumb 16 and is received through bores (not shown) in opposing side linkages 52 and 54 of the middle left phalange 36. It is also secured to the side linkage 52 of the middle left phalange 36 by an appropriate set screw 200. The outer brake rod 190 further becomes tapered as it extends from the side linkage 52 of the middle left phalange 36 and has a series of external outer rod threads 202. The threads 202 form a thread pattern which is substantially similar to the triple threaded screw thread pattern discussed above. The threads 202 advantageously, but not necessarily, begin adjacent to the inner radial surface 198 of the outer brake pulley 186 and terminate adjacent to the side linkage 54 of the middle left phalange 36.

The outer left brake 188 includes an outer left brake disc 204 which has a substantially circular body 206 formed integral with an outer left brake arm 208. Like the inner left brake 136, it, therefore, substantially resembles a common frying pan. The outer brake disc 204 is disposed around the portion of the outer brake rod 190 which has the outer rod threads 202. It defines a centrally located bore which has a series of internal brake threads 210 that can mate with and, thereby, engage the outer rod threads 202. The internal brake threads 210, therefore, form a thread pattern that is substantially similar to the triple threaded screw pattern discussed above. However, the length of thread pattern formed by the brake threads 210 is again smaller than the length of thread pattern formed by the outer rod threads 202. Therefore, the outer brake disc 204 can be threaded along the outer brake rod 190 and into engagement with the inner radial surface 198 of the outer brake pulley 186. This provides a braking force which can restrain the rotation of the outer brake pulley 186.

Like the inner brake arm 156, the top portion 212 of the outer brake arm 208 defines an axial opening for securely receiving an outer arm rod 214 that has an outer arm roller 216 preferably rotatably disposed around it. In like manner to the inner left brake 136, the outer left brake 188 also advantageously includes an oppositely disposed pair of outer left biasing elements 218 and 220, which can be suitable helical springs. The biasing element 218 has one of its ends secured to the top portion 212 of the outer brake arm 208 and its other end secured to the side linkage 54 of the middle left phalange 36. The biasing element 220 has one of its ends secured to the top portion 212 of the outer brake arm 208, while its other end is secured to the side linkage 52 of the middle left phalange 36.

As shown in FIG. 5, the outer left brake 188 occupies an equilibrium or rest position similar to that occupied by the inner left brake 136. Thus, in this equilibrium position, the biasing element 220 exerts a threshold initial tensile or pulling force on the outer brake arm 208. This tensile or pulling force maintains the outer brake disc 204 in its equilibrium state of engagement with the outer rod threads 202. This in turn provides the outer brake disc 204 with a threshold braking force that is initially exerted on the inner radial surface 198 the of outer brake pulley 186. The outer brake pulley 186 is, therefore, restrained from rotating clockwise relative to the outer brake rod 190.

As will become evident from later discussion, the outer brake disc 204 will not further engage the outer rod threads 202, and thereby will not move further inward against the inner radial surface 198 of the pulley 186, until any force incident on the outer arm roller 216 is sufficient to move the outer brake arm 208 downward. This force will also have to overcome the threshold restoring force of the biasing element 220. In the event that there is sufficient force, the outer brake arm 208 will move downward and the outer brake disc 204 will further engage the outer rod threads 202. Thus, the braking force against the outer brake pulley 186 will augment above its threshold level and, thereby, further resist rotation of the outer brake pulley 186. The braking force will tend to be the greatest whenever the force incident on the outer arm roller 216 has caused the biasing element 218 to become substantially fully compressed or simply when the outer brake disc 204 cannot move further inward.

As with the inner left brake 136, it is also desirable to ensure that the outer left brake 188 return substantially fully to its equilibrium position shown in FIG. 5. In like manner, therefore, the biasing element 220 of the outer brake 188 serves to provide an additional force for counteracting any remnant frictional forces between the outer brake pulley 186 and the outer brake disc 204.

Like the inner left brake 136, the outer left brake 188 also has a similar outer tendon brake pin 222 secured by a suitable screw pin 224. (See FIG. 4.) The tendon brake pin 222 defines an outer tendon cavity 226 which is situate adjacent to the outer surface 228 of the outer brake pulley 186. Moreover, the outer left brake 188 can also include a suitable outer left friction plate 230 which is disposed around the outer brake rod 190. The plate 230 is substantially similar to the friction plate 180 associated with the inner left brake 136 and is interposed between the outer brake disc 204 and the friction pad 196 associated with the outer brake pulley 186. The plate 230 also has a similar hollow friction stem 232 which protrudes toward the outer left joint 74 and is slidably connected to a slender, tertiary brake pin 234. The tertiary brake pin 234 is similar to the secondary brake pin 184 of the inner brake 136 and is connected to the side linkage 54 of the middle left phalange 36. It also functions similar to that of the secondary brake pin 184.

As with the inner left brake 136, it will be appreciated that the particular type of biasing elements 218 and 220 and other components of the outer shape adaption mechanism 132 chosen will depend upon the dynamics of the left thumb 16 and the particular task to be accomplished. However, the biasing elements 218 and 220 again preferably have the requisite force characteristics to permit the desired controlled pitching or pivoting referred to above.

Similar to the left thumb 16, the right thumb 18 includes outer, middle and inner right thumb phalanges or linkages 238, 240 and 242 which together are coupled to a right thumb base or base linkage 244. (See FIGS. 2 and 12-13.) The right phalanges 238, 240 and 242 and the right base linkage 244 are interconnected similar to the manner in which their counterpart left thumb phalanges 34, 36 and 38 and left base linkage 40 are interconnected. Likewise, the right thumb base 244 includes an oppositely disposed pair of somewhat knuckle shaped right links 246 and 248 that are securely seated on a right base plate 250 that has a substantially circular cross-section. (See FIG. 3(a).)

As more fully discussed below, the right thumb base 244 is connected to the right thumb engagement subassembly 24 so as to permit the right thumb 18 to yaw, roll and pitch or pivot relative to three separate right thumb axes running through the right thumb base 244. With reference to FIG. 3(a), it will be observed that the axis passing vertically through the right thumb base 244 corresponds to the axis relative to which the right thumb 18 yaws (hereinafter, "right thumb base yaw axis".) The axis passing horizontally through the right thumb base 244 which is associated with rolling of the right thumb 18 (hereinafter, "right thumb base roll axis".) The remaining axis, which is substantially orthogonal to the transverse axis of the right thumb 18 in its fully extended position shown in FIG. 2, is associated with pitching or pivoting of the right thumb 18 (hereinafter, "right thumb pitch or pivoting base axis".) It preferably moves along with the right thumb 18 when it yaws. Similar to the left thumb base axes, the right thumb base axes are advantageously, but not necessarily, mutually orthogonal to each other. The configuration and construction of the right thumb 18 is similar to that described above for the left thumb 16. Thus, it will be understood that the right thumb 18 would also appear as shown in FIGS. 4-5 and, thereby, have similar outer, middle and inner base, right thumb joints, inner and outer right shape adaption mechanisms and other similar components.

Similar to the thumbs 16 and 18, the finger 14 includes outer, middle, and inner finger phalanges 262, 264 and 266 which together are coupled to a finger base or base linkage 268. The finger phalanges 262, 264 and 266 and finger base linkage 268 are interconnected similar to the manner in which their counterpart left phalanges 34, 36 and 38 and left linkage 40 are interconnected. Likewise, the finger base linkage 268 includes a pair of oppositely disposed somewhat knuckle shaped finger links 270 and 272 that are securely seated on a finger base plate 274 that has a substantially circular cross-section. The links 270 and 272 can also be joined together and formed integral with a face plate 276. (See FIG. 3(b).)

As more fully discussed below, the finger base linkage 268 is connected to the finger engagement subassembly 26 so as to permit the finger 14 to yaw and pitch or pivot relative to two separate finger base axes running through the finger base 268. With reference to FIG. 3(b), it will be observed that the axis passing vertically through the finger base 268 corresponds to the axis relative to which the finger 14 yaws (hereinafter, "finger yaw base axis".) The remaining axis, which is substantially orthogonal to the transverse axis of the finger 14 in its fully extended position (shown in FIG. 2), is associated with pitching or pivoting of the finger 14 (hereinafter, "finger pitch or pivoting base axis".) It preferably moves along with the finger 14. The finger base axes are advantageously, but not necessarily, mutually orthogonal to each other. The configuration and construction of the finger 14 is similar to that described above for the left thumb 16. Thus, the finger 14 would also appear as shown in FIGS. 4-5 and, thereby, have similar outer, middle and inner or base right thumb joints, inner and outer finger shape adaption mechanisms and other similar components.

In accordance with another feature of the invention, the engagement sub-assemblies 22 and 24 selectively cause the thumbs 16 and 18 respectively to engage in yawing, rolling and pitching or pivoting motions and versatilely assume multiple configurations. Further, the engagement sub-assembly 26, selectively causes the finger 14 to engage in yawing and pitching or pivoting motions, and versatilely assume multiple configurations. As set forth below, each sub-assembly 22, 24 and 26 has an assemblage of shafts, gears, motors and tendons that accomplish the engagement aforementioned functions.

More specifically, and with reference first to engagement of the left thumb 16, the left sub-assembly 22 includes a left thumb, primary drive shaft 300 and a left thumb, secondary drive shaft 302 which is substantially concentric with and rotatably disposed around the left primary shaft 300. (See FIG. 3(c).) The left primary and left secondary shafts 300 and 302 are oriented such that their common transverse axis is substantially parallel to the transverse axis of the left thumb 16 in its fully extended or rest position shown in FIG. 2. Their common transverse axis is also substantially parallel to the left thumb base axis associated with rolling motion of the left thumb 16. (See FIG. 3(c).)

For the purpose of inducing yawing motion of the left thumb 16, the left sub-assembly 22 includes a left yaw motor 304 and a left yaw gear sub-assembly 306. As depicted in FIG. 3(c) the left yaw motor 304 is rotatably connected near one end of the left primary shaft 300 and can rotate the shaft 300 in either a clockwise or counterclockwise direction. It can also be mounted within or surrounded by, a suitable left yaw motor housing 307. (See FIGS. 1 and 11.) The motor 304 can be any suitable dc or stepper motor or any other motor that can provide the requisite actuation of the left primary shaft 300.

The left yaw gear sub-assembly 306 has a left thumb yaw worm gear 308 which is engageable with a left thumb yaw worm 310. The left yaw worm gear 308 is mounted on a left linkage shaft 312 for rotation with the left linkage shaft 312. The top portion of the left linkage shaft 312, protrudes through an aperture (not shown) in the left thumb base 40 and is secured to the left thumb base 40. (See FIGS. 3(c) and 11.) Consequently, the left thumb base 46 is movable along with the left linkage shaft 312. When so secured, the transverse axis of the shaft 312 is substantially parallel to the left thumb base axis associated with yawing motion of the left thumb 16. The left yaw worm 310 is mounted for rotation near the remaining free end of the left primary shaft 300. It, therefore, has its transverse axis oriented substantially parallel to the common transverse axis of the left primary and secondary shafts 300 and 302.

Upon actuation by the left yaw motor 304, the left primary shaft 300 rotates and, thereby, causes the left yaw worm 310 to engage the left yaw worm gear 308. This engagement substantially simultaneously induces the left linkage shaft 300 and left thumb base 40 to rotate together with the left yaw worm gear 308. Consequently, the left thumb 16 yaws in a plane substantially orthogonal to the transverse axis of the linkage shaft 312. Relative to its fully extended or rest position shown in FIG. 2, the left thumb 16 can also yaw in a plane that is substantially parallel to the plane in which the left primary and left secondary shafts 300 and 302 are located. That is, it yaws about the left thumb base axis associated with yawing motion. (See FIG. 3(c).)

For the purpose of inducing rolling motion of the left thumb 16, the left sub-assembly 22 further includes a left roll motor 314 and a left roll gear sub-assembly 316. The left roll motor 314 has a left roll shaft 318 which is rotatably connected to it and can rotate the shaft 318 in either a clockwise or counterclockwise direction. It can also be surrounded by a suitable left roll motor housing 319. (See FIGS. 1 and 10.) The motor 314 can be any suitable dc or stepper motor or any other motor that can provide the requisite actuation of the left roll shaft 318 so as to drive the left roll sub-assembly 316. The transverse axis of the left roll shaft 318 is oriented substantially orthogonal to the common transverse axis of the left primary and secondary shafts 300 and 302.

Figure 9:
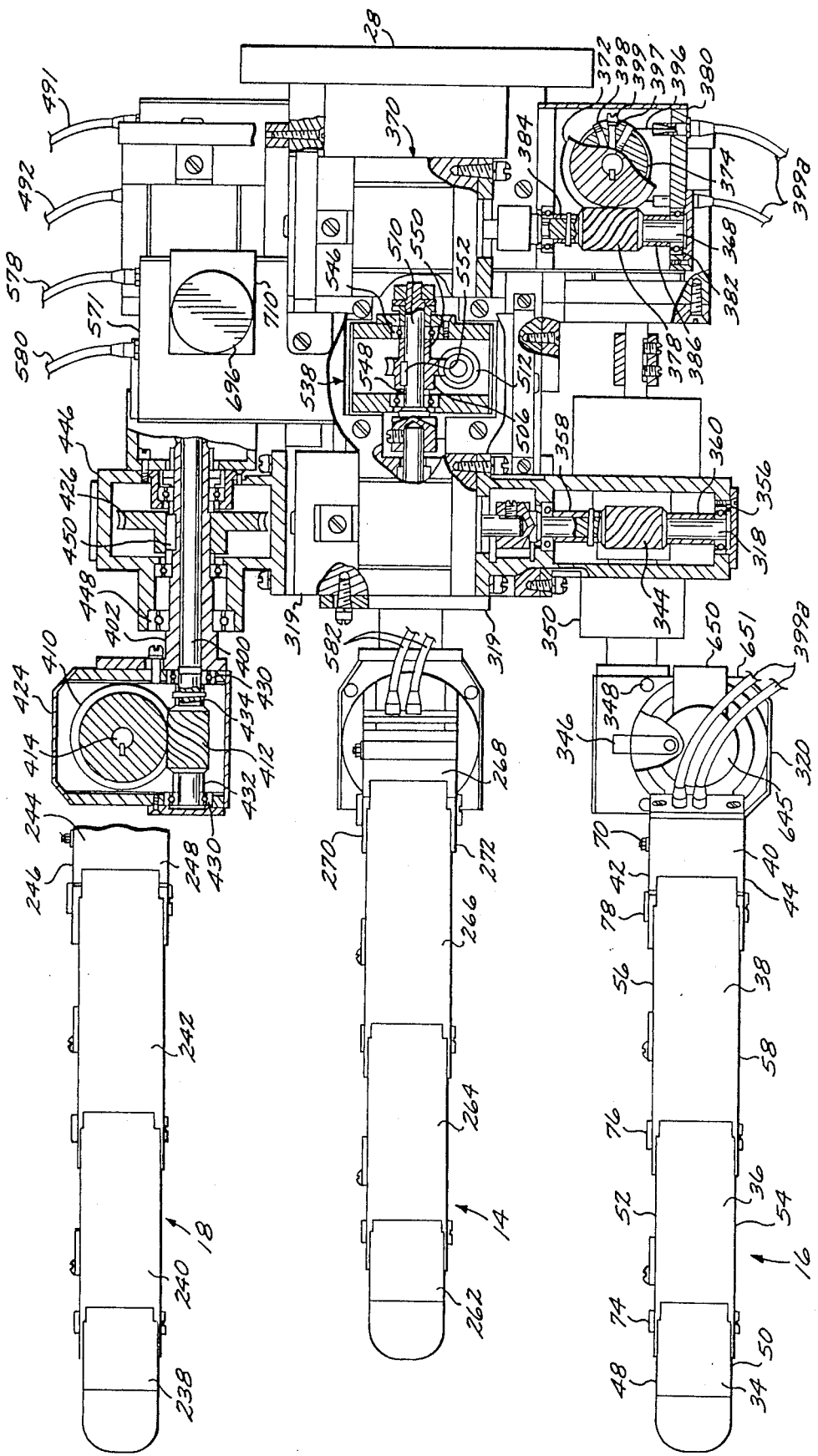
FIG. 9 is an enlarged top view of the artificial dexterous hand of the present invention with selected features illustrated by way of cut-away views.

The left roll gear sub-assembly 316 includes a left roll housing 320, which is secured to one end of the left secondary shaft 302, and a left roll worm gear 322, which is secured to the left secondary shaft 302 toward the other end of the left secondary shaft 302. The housing 320 surrounds the left yaw gear sub-assembly 306 and helps stabilize the left yaw gear sub-assembly 306 and otherwise enhances the operational characteristics of the left thumb 16. As depicted in FIGS. 3(c), 9 and 11, it further defines a side aperture 324 for receiving the left primary shaft 300 and a top aperture (not shown) for receiving the left linkage shaft 312. As such, the left thumb base 40 is substantially contiguous with the top surface of the left roll housing 320. (See FIG. 3(c).)

Suitable bearings 326 can also be situated between the housing 320 and left primary shaft 300 in order to stabilize the shaft 300. (See FIG. 10.) In that case, suitable sleeves 328 and 330 can be disposed around the shaft 300 in order to strengthen it and better retain the bearings 326. Suitable upper and lower bearings 332 and 334 can further be situated between the housing 320 and the left linkage shaft 312 in order to better stabilize the shaft 312 during operation. (See FIG. 11.) To a similar end, thrust or other suitable bearings 336 can be located between the housing 320 and left thumb base 40. A suitable nut 338 can also be attached to the bottom of the left linkage shaft 312 in order to maintain the lower bearings 334 in the housing 320. Moreover, the left linkage shaft 312 can be associated with a suitable key 340 for facilitating torque transmission between the left yaw worm gear 308 and the left linkage shaft 312.

The left roll worm gear 322 defines a centrally disposed left roll bore 342 for permitting the left primary shaft 300 to pass through it to the left yaw motor 304. The left roll worm gear 344 is also engageable with a left roll worm 344 that is mounted for rotation with the left roll shaft 318. As shown in FIG. 9 the left roll housing 320 can also be associated with an elongated yaw limit plate 346 that is connected to the left thumb base 40. It serves to limit the degree of yawing of the thumb 16 upon contact with a limit pin 348 that protrudes from the top of the housing 320.

Upon actuation by the left roll motor 314, the left roll worm 344 engages the left roll worm gear 322 such that the left secondary shaft 302 rotates with the left roll housing 320 about the common transverse axis of the left primary and secondary shafts 300 and 302. At the same time, the housing 320 carries along the left thumb base 40. Consequently, the left thumb 16 rolls in a plane substantially orthogonal to the common transverse axis of the left primary and secondary shafts 300 and 302. That is, it rolls relative to the left thumb base axis associated with rolling motion. (See FIG. 3(c).)

It will be observed that the left thumb 16 is capable of rolling at least substantially 180 in either a clockwise or counterclockwise direction in light of the reversibility of the left roll motor 314. Thus, in the event that the left thumb 16 were initially in the extended or rest position shown in FIG. 2, it would rotate substantially ninety degrees to assume the roll position shown in FIG. 1. As viewed from the frame of reference of an observer sitting on the sphere 12 and viewing the thumb 16, the rotation would be clockwise. Conversely, the thumb 16 would rotate counterclockwise to reassume its previous position. It will further be observed that the left primary and secondary shafts 300 and 302, left yaw gear sub-assembly 306 and left roll gear sub-assembly 316 together effectively cooperate as one preferred form of a left thumb yaw and roll gear sub-assembly that causes yawing and rolling of the left thumb 16.

In like manner to the left yaw gear sub-assembly 306, the left roll gear sub-assembly 316 can be surrounded by a suitable housing 350 that is itself secured to the left roll motor housing 319. (See FIGS. 1, 9–10.) In that event, suitable bearings 352 can be situated between the housing 350 and the left secondary shaft 302. (See FIG. 10.) Further, the left secondary shaft 302 can be associated with a suitable key 354 for facilitating torque transmission with the left roll worm gear 322. Suitable bearings 356 can further be situated between the left roll shaft 318 and the housing 350. In that event, sleeves 358 and 360 can also be disposed about the shaft 318 on opposing sides of the left roll worm 344 in order to strengthen the shaft and better retain the bearings 356. (See FIG. 9.) It will be understood that the aforementioned additional features tend to enhance the overall stability and operational characteristics of the left thumb 16.

For the purpose of inducing pivoting or pitching motion of the left thumb 16, the left engagement subassembly 22 further includes a left pitch motor 362 which actuates a left thumb tendon or cable 364 through driving a left thumb pitch gear sub-assembly 366. (See FIG. 3(c).) The left pitch motor 362 has a left pitch shaft 368 which is rotatably connected to it and can rotate the pitch shaft 368 in either a clockwise or counterclockwise direction. It can also be surrounded by a suitable left pitch motor housing 370. (See FIGS. 1 and 9.) The motor 362 can be any suitable dc or stepper motor or any other motor that can provide the requisite actuation of the left pitch shaft 368 so as to drive the left pitch sub-assembly 366. The transverse axis of the left pitch shaft 368 is oriented substantially orthogonal to the common transverse axis of the left pitch primary and secondary shafts 300 and 302. The left pitch shaft 368 further lies in a plane substantially parallel to the plane in which the shafts 300 and 302 are located.

The left pitch gear sub-assembly 366 has a left pitch worm gear 372 which is substantially contiguous with a left reducer drum 374. (See FIGS. 3(c), 9, and 14.) Both the left pitch worm gear 372 and left reducer drum 374 are mounted for rotation with a left reducer shaft 376. The left worm gear 372 is engageable with a left pitch worm 378 that is mounted for rotation on the left pitch shaft 368. (See FIGS. 3(c) and 9.) As such, the left reducer shaft 376 has its transverse axis oriented substantially orthogonal to the transverse axis of the left pitch shaft 368.

The left pitch gear sub-assembly 366 can also be provided with additional features which enhance the stability and operational characteristics of the left thumb 16 and left pitch sub-assembly 366. More specifically, the left pitch sub-assembly 366 can be surrounded by a suitable left reducer housing 380 which is itself secured to the left pitch motor housing 370. (See e.g. FIGS. and 9.) Suitable bearings 382 can also be situated between the housing 380 and the left pitch shaft 368. Suitable sleeves 384 and 386 can further be disposed around the left pitch shaft 368 on opposing sides of the left pitch worm 378 to strengthen the shaft 368 and retain the bearings 382. (See FIG. 9.)

Likewise, suitable upper and lower bearings 388 and 390 can be situated between the left reducer shaft 376 and the housing 380 to stabilize the shaft 376. (See FIG. 14.) The upper and lower bearings 388 and 390 can also be retained within the housing 380 by appropriate washers or nuts 391 and 392 connected near opposing end portions of the left reducer shaft 376. (See FIG. 14.) Moreover, the left reducer shaft 376 can also have suitable keys 393 for facilitating torque transmission between the shaft 376 and the left drum 374 and left pitch worm gear 372. The left drum 374 and left pitch worm gear 372 can also be better mounted for rotation with each other by a suitable screw 394 threaded through co-axial bores (not shown) in the left drum 374 and left pitch worm gear 372. When so threaded, the transverse axis of the screw 394 is substantially parallel to the left reducer shaft 376. (See FIG. 14.)

The left thumb tendon 364 is wrapped around the left reducer drum 374 and connected to the left thumb 16 in a manner that permits pitching or pivoting not only of the left thumb 16 at its inner or base left joint 78 but also of the left thumb phalanges 34, 36 and 38 relative to each other. More specifically, as shown in FIG. 3(c) the left thumb tendon 364 wraps around the left reducer drum 374 for a plurality of revolutions in such a way that it forms upper and lower left leads 395 and 396 that extend from the drum 374 to the left thumb 16 through bores (not shown) in the left reducer housing 380. (See e.g. FIGS. 1 and 3(c).)

Moreover, the left drum 374 can further be partially surrounded by an arcuate plate 397 which assists in retaining the left thumb tendon 364 on the left drum 374. (See FIGS. 9, 14.) The plate 397 and outer surface of the drum 372 define an arcuate channel and the plate 397 is secured to the drum by pins 398 and a screw 399.

Both leads 395 and 396 pass along the exterior of the hand and enter the interior of the left thumb 16 through bores (not shown) in the left thumb base linkage 40. (See e.g. FIGS. 1, 3(c) and 9.) The portion of the left thumb tendon 364 that extends between the exterior of the left thumb 16 and the left reducer housing 380 can also be surrounded by an appropriate tubular casings 399a for preserving the useful life of the left tendon 328 (casings only partially shown in FIGS. 4 and 9–10.)

The upper lead 395 first contacts or is received by the underside of the left link pulley 72 which serves to guide the upper lead 395 into proper contact with the inner left pulley 108. The upper lead 395 then wraps successively around the inner, middle and outer left pulleys 108, 92 and 80 in a counterclockwise wrapping direction before terminating at the left tendon pin 66 to which it is firmly secured. It will be observed that the wrapping is initiated around the top of the outer surface of each of the pulleys 108, 92 and 80. (See FIG. 5.)

As depicted in FIG. 5, the lower lead 396 first contacts the underside of the outer surface of inner left pulley 110 and wraps around the pulley 110 in a clockwise wrapping direction. It then contacts the upper surface of the inner arm roller 164 associated with the inner brake arm 156 and wraps around the inner brake pulley 134 in a counterclockwise wrapping direction. Thereafter, the lower lead 396 contacts the underside of middle left pulley 94 and wraps around the middle left pulley 94 in a clockwise wrapping direction. It will be observed that the wrapping process around the inner brake pulley 134 begins with the lower lead 396 contacting the top of the outer surface of 172 the pulley 134. On the other hand, the wrapping process around the underside of the outer surface of the middle left pulley 94 begins with the lower lead 396 contacting the underside of the pulley 94.

Afterwards, the lower lead 396 contacts the upper surface of the outer arm roller 216 associated with the outer brake arm 208 and winds around the outer surface 228 of outer brake pulley 186 in a counterclockwise wrapping direction. Again, it will be observed that the wrapping process begins with the lower lead 396 being received by the top of the outer surface 228 of the outer brake pulley 186. Finally, the lower lead 396 wraps around the underside of the outer surface of the outer left pulley 80 before terminating at the left tendon pin 66 to which it is firmly secured.

It will be appreciated that the lower lead 396 can be affixed to the inner brake pulley 134 and outer brake pulley 186 by inserting it through the inner and outer left tendon cavities 178 and 226 in the inner and outer tendon brake pins 170 and 222 respectively. This will tend to minimize undesirable slippage of the lower lead 396. The left thumb tendon is preferably a suitable sheathed cable. It will be, however, be appreciated that the left thumb tendon 364 can be any suitable tendon, cable or cord which has the requisite strength and tautness for proper pivoting and retraction of the left thumb 16 and its respective left thumb phalanges 34, 36 and 38. Each of the leads 395 and 396 can also be wrapped around the various pulleys in other ways that achieve the desired pitching and retraction of the left thumb 16 in accordance with the invention.

Upon actuation by the left pitch motor 362, the left pitch worm 378 engages the left pitch worm gear 372, thereby causing the left reducer drum 374 to rotate about the transverse axis of the left reducer shaft 376. Since the left pitch motor 362 can rotate the left pitch shaft 368 in either a clockwise or counterclockwise direction, the left reducer drum 374 can similarly rotate either clockwise or counterclockwise. As evident from FIG. 3(c), clockwise rotation of the left reducer drum 374 would apply tension to the upper lead 395. This would cause the upper lead 395 to tend to wrap further around the left drum 374 and the lower lead 396 to tend to uncoil from it. Consequently, and as discussed more fully later, the left thumb 16 would be retracted. Relative to the configuration of the left thumb 16 shown in FIG. 1, the retraction would commence at the outer left phalange 34. Conversely, when the left drum 374 rotates in a counterclockwise direction, it would apply tension to the lower lead 396. Therefore, the lower lead 396 would tend to wrap further around the left drum 374 while the upper lead 395 would tend to uncoil from it. Consequently, and as discussed below, the left thumb 16 and its corresponding phalanges 34, 36 and 38 would pitch or pivot.

The particular manner in which the inner and outer shape adaption mechanisms 130 and 132 control the sequence of pitching or pivoting of the left phalanges 34, 36 and 38 will now be discussed with reference to certain exemplary pivoting or pitching situations. More specifically, consider the following first situation: The left thumb 16 is in a fully extended configuration, such as that shown in FIG. 2. Further, it is desired that the left thumb 16 pivot or pitch relative to inner base joint so as to place itself in a position more suitable for grasping and manipulating a certain object. Moreover, at the time the desired pivoting or pitching is to be initiated, the left thumb 16 is not yet in contact with the object.

In that event, the left pitch motor 362 will actuate the left reducer shaft 376 to rotate the left reducer drum 374 in a counterclockwise direction. The lower lead 396, therefore, will begin to be tensioned and the upper lead 395 slackened. This tensile force would propagate along the lower lead 396 to the inner pulley 110 of the inner base joint 78. At the same time, the other inner pulley 108 will experience a reduction in tensile force from the upper lead 395. Consequently, the inner, middle and left phalanges 34, 36 and 38 as a whole would together pitch or pivot downward relative to the left thumb base 40 and the inner pulleys 108 and 110 will tend to rotate somewhat in a counterclockwise direction.

It will be observed that the aforementioned tensile force will also propagate along the lower lead 396 to the inner shape adaption mechanism 130. Thus, the inner brake pulley 134 will experience a tensile force urging it to rotate clockwise. Moreover, the tensile force will give rise to a downward force. This downward force will become incident on the inner arm roller 164 and, consequently, on the inner brake arm 156 of the inner brake disc 152. The tensile force exerted on the inner brake pulley 134 will however, be counteracted by the threshold braking force exerted on the inner radial surface 146 of the inner brake pulley 134.

The threshold braking force will generally be sufficient to overcome the aforementioned tensile force such that the inner brake pulley 134 will not rotate. The absence of clockwise rotation of the inner brake pulley 134 will thereby prevent the propagation of sufficient tensile force to accomplish pivoting of the outer, middle, inner and left phalanges 34, 36 and 38 relative to each other. It will further be understood that, if the aforementioned tensile force were somehow sufficient to cause the inner brake arm 156 to pivot downward, the inner brake disc 152 will apply increasing braking force against the inner radial surface 146 of the inner brake pulley 134. The resulting augmented braking force would advantageously sufficiently counteract the tensile force so as to still prevent rotation of the inner brake pulley 134.

Consider now, that it is desired to retract the thumb 16 so that it can reassume its initial configuration. In that event, the left pitch motor 362 will be reversed and, thereby, cause the left reducer drum 374 to rotate in a clockwise direction. Tensile force will then propagate along the upper lead 395, while the lower lead 396 will slacken. The inner left pulleys 108 and 110 will, therefore, rotate in a clockwise direction. The outer, left and middle phalanges 34, 36 and 38 as a whole would then pitch or pivot upward and the inner pulleys 108 and 110 would tend to rotate in a clockwise direction. The left thumb 16 would thereby reassume its initial configuration. It will be observed that the above described controlled sequential pivoting advantageously prevents the phalanges 34, 36 and 38 from undesirably pivoting or pitching arbitrarily relative to each other.

Consider the following second situation: As the left phalanges 34, 36 and 38 as a whole begin to pitch or pivot downward relative to the inner base linkage 40, the area of the left thumb 16 between the middle and base joints 76 and 78 is obstructed by an object. In that event, the left pitch motor 362 will cause the left reducer drum 374 to exert increasing tensile force on the lower lead 396 to attempt to counteract the force exerted by the object in the aforementioned area. This tensile force will again propagate to both the inner left pulley 134 and the inner shape adaption mechanism 130 as described above. As the tensile force increases, it will become sufficient enough to move the inner brake arm 156 increasingly downward. The inner brake disc 152 will, therefore, exert increasing braking force against the inner radial surface 146 of the inner brake pulley 134.

This resulting augmented braking force will increasingly counteract the increasing tensile force until the biasing element 166 is substantially fully compressed or simply until the inner brake disc 152 cannot move further inward along the inner brake rod 138. Eventually, the tensile force will overcome the augmented braking force. The inner brake pulley 134 will then rotate clockwise. Thus, eventually sufficient tensile force will propagate to the middle left pulley 94 so as to cause the middle left phalange 36 to pivot or pitch downward relative to the inner left phalange 38. Further, the middle left pulleys 92 and 94 will tend to rotate counterclockwise. The middle left phalange 36 will then continue to pivot around the object until the object obstructs further movement of the phalange 36 by exerting force in the area between the outer and middle left joints 74 and 76. It will be understood that during this process the middle left pulley 92 will rotate counterclockwise in light of the slackened condition of the upper lead 395.

Since further movement of the middle left phalange 36 is now obstructed, the left pitch motor 362 will provide increasing tensile force to the lower lead 396 so as to counteract the force exerted by the object in the immediately aforementioned area. This increasing tensile force will propagate to the outer shape adaption mechanism 132 which will then function similarly to the inner shape adaption mechanism 130. That is, the outer brake pulley 186 will not begin to rotate clockwise until the tensile force has exceeded the resulting augmented braking force applied by the outer brake disc 204 against the inner radial surface 198 of the outer brake pulley 186.

At that point, the outer brake pulley 186 will rotate clockwise. Consequently, sufficient tensile force will propagate to the outer left pulley 80 for the outer left phalange 34 to pitch or pivot downward relative to the middle left phalange 36 until the outer left phalange 34 contacts the object. Correspondingly, the outer left pulley 80 will tend to rotate counterclockwise. It will be appreciated that above described controlled sequential pitching or pivoting of the phalanges will result in the left thumb 16 versatilely configuring itself so as to properly grip and thereafter manipulate the object.

Suppose now that it is desired to retract the left thumb 16 such that it assumes its initial fully extended configuration. Again, the left pitch motor 362 will be reversed. The lower lead 396 will then slacken, while tensile force will be exerted on the upper lead 395. As a result, the outer left phalange 34 would pitch or pivot upward relative to the middle left phalange 36. The upward movement will continue until the outer left phalange 34 assumes its initial configuration relative to the middle left phalange 36. Thereafter, the outer and middle left phalanges 34 and 36 as a whole will pitch or pivot upward relative to the inner left phalange 38. This upward movement will continue until the outer and middle left phalanges 34 and 36 assume their initial configuration relative to the inner left phalange 38. Finally, the outer, middle and inner left phalanges 34, 36 and 38 as a whole will pivot or pitch upward relative to the left thumb base 40 until the left thumb 16 assumed its initial configuration. It will be observed that during the retraction process the various pulleys would also rotate in directions opposite to their respective directions of rotation during the above described pivoting or pitching process.

Consider now the following third situation: The left thumb 16 has assumed the pitching or pivoting configuration described in the first situation and an object then contacts the area of the thumb located between the outer and middle left joints 74 and 76. In that event, the left pitch motor 362 will cause the left reducer drum 374 to rotate counterclockwise. Thus, it will exert increasing tensile force on the lower lead 396 to attempt to counteract the force exerted by the object in the aforementioned area. This tensile force will propagate to the outer shape adaption mechanism 132. Eventually, the increasing tensile force will overcome the augmented brake force. Thus, as described above for the second situation, the outer left phalange 34 will pivot or pitch downward relative to the middle left phalange 36. However, the middle left phalange 36 will not pivot or pitch relative to the inner left phalange 38. It will be understood that retraction of the outer phalange 34 relative to the middle phalange 38 will occur in the manner described for situation two above.

Turning now to the engagement of the right thumb 18, the right thumb sub-assembly 24 is constructed essentially similar to that of the left thumb engagement sub-assembly and has similar operational characteristics. (See FIGS. 1, 3(a), 9, 12 and 14.) It includes a right thumb primary drive shaft 400 and a right thumb secondary drive shaft 402 which is concentric with and rotatably disposed around the right primary shaft 400 (see FIG. 3(a).) The right primary and right secondary shafts 400 and 402 are oriented such that their common transverse axis is substantially parallel to the transverse axis of the right thumb 18 in its fully extended rest position shown in FIG. 2. Their common transverse axis is also substantially parallel to the right thumb base axis associated with rolling motion of the right thumb 18. (See FIG. 3(a).) Further, the right primary and right secondary shafts are situated in essentially the same plane as the left primary and left secondary shafts 300 and 302.

For the purpose of inducing yawing motion of the right thumb 18, the right thumb engagement sub-assembly 24 includes a right yaw motor 404 and a right yaw gear subassembly 406. As depicted in FIG. 3(a), the right yaw motor 404 is rotatably connected to the right primary shaft 400 near one end of the shaft 400 and can rotate the shaft 400 in either a clockwise or counterclockwise direction. The motor 404 can also be surrounded by, or mounted within, a suitable right yaw motor housing 408. (See FIGS. 2 and 14.) It can also be any suitable dc motor or any other motor that can furnish the requisite actuation of the right primary shaft 400.

The right yaw gear sub-assembly 406, has a right thumb yaw worm gear 410 which is engageable with a right thumb yaw worm 412. The right yaw worm gear 410 is mounted on a right linkage shaft 414 for rotation with the right linkage shaft 414. The top portion of the right linkage shaft 414 protrudes through an aperture (not shown) in the right thumb base 244 and is secured to the right thumb base 244. (See FIGS. 3(a) and 14.) When so secured, the transverse axis of the right linkage shaft 414 is substantially parallel to the right thumb base axis associated with yawing motion of the right thumb 18. Consequently, the right thumb base 244 is movable with the right linkage shaft 414 about the yaw axis of the right thumb base 244. It, therefore, has its transverse axis oriented substantially parallel to the common transverse axis of the right primary and secondary shafts 400 and 402.

Upon actuation by the right yaw motor 404, the right primary shaft 400 rotates and, thereby, causes the right yaw worm 412 to engage the right yaw worm gear 410. This engagement substantially simultaneously causes the right linkage shaft 414 and right thumb base 244 to rotate along with the right yaw Worm gear 410. Consequently, the right thumb 18 yaws in a plane substantially orthogonal to the transverse axis of the right linkage shaft 414. Relative to its rest position shown in FIG. 2, the right thumb 18 can also yaw in a plane substantially parallel to the common plane in which the shafts 400 and 402 are located. That is, it yaws about the right thumb base axis associated with yawing motion. (See FIG. 3(a).)

For the purpose of inducing rolling motion of the right thumb 18, the right thumb engagement sub-assembly 24 further includes a right roll motor 416 and a right roll gear sub-assembly 418. The right roll motor 416 has a right roll shaft 420 which is rotatably coupled to it and can rotate the shaft 420 in either a clockwise or counterclockwise direction. It can also be surrounded by, or mounted within, a suitable right roll motor housing 422. (See e.g. FIGS. 1-2.) The motor can be any suitable dc or stepper motor or any other motor that can provide the requisite actuation to the right roll shaft 420 so as to drive the right roll sub-assembly. The transverse axis of the right roll shaft 420 is oriented substantially orthogonal to the common transverse axis of the right primary and secondary shafts 400 and 402. The right roll shaft 420 also lies in a plane that is substantially parallel to the common plane in which the shafts 400 and 402 are located.

As shown in FIGS. 1, 9, 12 and 14 the right roll gear sub-assembly 24 includes a right roll housing 424, which is secured to one end of the right secondary shaft 402, and a right roll worm gear 426, which is secured to the right secondary shaft 402 toward the other end of the shaft 402.

The right roll housing 424 surrounds the right yaw gear sub-assembly 406 and helps stabilize the right yaw gear sub-assembly 406 and otherwise enhances the operational characteristics of the right thumb 18. As depicted in FIG. 3(a), it further defines a side aperture 428 for receiving the right primary shaft 400 and a top aperture (not shown) for receiving the right linkage shaft 414. As such, the right thumb base 244 is substantially contiguous with the top surface of the right roll housing 424. Unlike the left roll housing 320, however, the side aperture 428 of the right roll housing 424 is located along the rear of the side 429 of the right roll housing 424.

Suitable bearings 430 can also be situated between the housing 424 and the right primary shaft 400 in order to stabilize the shaft 400. In that event, suitable sleeves 432 and 434 can be disposed around the shaft 400 and on opposing sides of the right yaw worm 412 in order to strengthen it and better retain the bearings 430. (See FIG. 9.) Suitable upper and lower bearings 436 and 438 can further be situated between the housing 424 and right linkage shaft 414 to better stabilize the shaft 414 during operation of the right thumb 18. (See FIG. 14.) A suitable nut 439 can also be affixed to the bottom of the shaft 414 in order to maintain the lower bearings 438 in the housing 424. Moreover, the right linkage shaft 414 can be associated with a suitable key 440 for facilitating torque transmission between the right yaw worm gear 410 and the right linkage shaft 414.

The right roll worm gear 426 defines a centrally disposed right roll bore 442 for receiving the right primary shaft 400 such that the shaft 400 passes through it to the right yaw motor 404. (See e.g. FIG. 3(a).) The right roll worm gear 426 is also engageable with a right roll worm 444 which is mounted for rotation on the right roll shaft 420. Similar to the left roll housing 320, the right roll housing 422 can be associated with a yaw limit plate and yaw limit pin that cooperate to limit the degree of yawing of the right thumb 18.

Upon actuation by the right roll motor 416, the right roll worm 444 engages the right roll worm gear 426 such that the right secondary shaft 402 rotates with the right roll housing 424 about the common transverse axis of the right primary and secondary shafts 400 and 402. Consequently, relative to its rest position shown in FIG. 2, the right thumb 18 rolls in a plane substantially orthogonal to the common transverse axis of the right primary and secondary shafts 400 and 402. That is, it rolls relative to the right thumb axis associated with rolling motion.

It will be observed that the right thumb 18 is capable of rolling at least substantially 180 in either a clockwise or counterclockwise direction in light of the reversibility of the right roll motor 416. Thus, in the event that the right thumb 18 was initially in its rest or extended position shown in FIG. 2, it would rotate substantially ninety degrees to assume the position shown in FIG. 1. As viewed from the frame of reference of an observer sitting on the sphere 12 and viewing the thumb 18, the rotation would be counterclockwise. Conversely, the thumb 18 would rotate clockwise to reassure its previous position. It will further be observed that the right primary and secondary shafts 400 and 402, right yaw gear sub-assembly 405 and right roll gear sub-assembly 418 together effectively cooperate as one preferred form of right thumb yaw and roll gear sub-assembly that causes yawing and rolling of the right thumb 18.

In like manner to the right yaw gear sub-assembly 406, the right roll gear sub-assembly 418 can be surrounded by a suitable housing 446 that is itself secured to the right roll motor housing 422 and to the support structure 28 generally. (See FIG. 1, 9 and 12.) In that event, suitable bearings 448 can be situated between the housing 446 and the right secondary shaft 402. (See FIG. 9.) Further, the right secondary shaft 402 can be associated with a suitable key 450 for facilitating torque transmission with the right roll worm gear 426.

Suitable bearings 452 can further be situated between the right roll shaft 420 and the housing 446 in a manner similar to that for the left roll shaft 318. (See FIG. 12.) In that event, sleeves 454 and 456 can also be disposed about the shaft 420 on opposing sides of the right roll worm 444 in order to strengthen the shaft 420 and better retain the bearings 452. It will be understood that the aforementioned additional features tend to enhance the overall stability and operational characteristics of the right thumb 18.

For the purpose of inducing pivoting or pitching motion of the right thumb 18, the right engagement sub-assembly 24 further includes a right pitch motor 458 which actuates a right thumb tendon or cable 460 through driving a right thumb pitch gear sub-assembly 462. As evident from comparing FIGS. 3(a) and (c), the right engagement sub-assembly 24 is constructed essentially similar to the left engagement sub-assembly 22. (See also FIGS. 9–12 and 14.) The right pitch motor 458 has a right pitch shaft 464 which is rotatably connected to it and can rotate the right pitch shaft 464 in either a clockwise or counterclockwise direction. It can also be surrounded by a suitable right pitch housing 466. (See e.g. FIG. 2.) The motor 458 can be any suitable dc or stepper motor or any other motor that can provide the requisite actuation of the right pitch shaft 464 so as to drive the right pitch sub-assembly 462. The transverse axis of the right pitch shaft 464 is oriented substantially orthogonal to the common transverse axis of the right primary and secondary shafts 400 and 402. The right pitch shaft 464 also lies in a plane which is substantially parallel to the common plane in which the shafts 400 and 402 are located.

The right pitch gear sub-assembly 462 is constructed essentially similar to the left pitch gear sub-assembly 366. (See FIGS. 3(a) and (c).) It has a right pitch worm gear 468 which is substantially contiguous with a right reducer drum 470. Both the right pitch worm gear 468 and right reducer drum 470 are mounted for rotation with a right reducer shaft 472. The right worm gear 468 is engageable with a right pitch worm 474 that is mounted for rotation on the right pitch shaft 464. As such, the right reducer shaft 472 has its transverse axis oriented substantially orthogonal to the transverse axis of the right pitch shaft 464.

The right pitch gear sub-assembly 462 can also be provided with additional features which enhance the stability and operational characteristics of the right thumb 18 and right pitch sub-assembly 462 particularly. More specifically, the right pitch sub-assembly 462 can be surrounded by a suitable right reducer housing 476 which is itself secured to the right pitch motor housing 466 and the support structure 28 generally. (See dotted lines in FIG. 2 and see FIG. 11.) In like manner to the left pitch shaft 368, suitable bearings can also be situated between the housing 476 and the right pitch shaft 464. Further, suitable sleeves can be disposed around the right pitch shaft 464 on opposing sides of the right pitch worm 474 to strengthen the shaft 464 and retain the bearings.

Likewise, suitable upper and lower bearings 480 and 482 can be situated between the right reducer shaft 472 and the housing 476 to stabilize the shaft 472. (See FIG. 11.) The upper and lower bearings 480 and 482 can also be retained within the housing 476 by appropriate washers or nuts 484 and 486 connected to opposing end portions of the shaft 472. Moreover, the right reducer shaft 472 can also have suitable keys 488 for facilitating torque transmission between the shaft 472 and the right reducer drum 470 and right pitch worm gear 468. The right drum 470 and right pitch worm gear 468 can also be better mounted for rotation with each other by a suitable screw 490 threaded through co-axial bores (not shown) in the right drum 470 and right pitch worm gear 468. When so threaded, the transverse axis of the screw 490 is substantially parallel to the right reducer shaft 472. (See FIG. 11.)

The right thumb tendon 460 is wrapped around the right reducer drum 470 and is connected to the right thumb 18 in a manner that permits pitching or pivoting not only of the right thumb 18 at its inner or base right joint but also of the right thumb phalanges 34, 36 and 38 relative to each other. It will be observed that the manner of wrapping and connecting the right thumb tendon 460 is similar to that employed for the left thumb tendon 364. (Compare FIGS. 3(a) and (c) and see FIGS. 4–5.) More specifically, as shown in FIG. 3(a) the right thumb tendon 460 wraps around the right reducer drum 470 for a plurality of revolutions in such a way that it forms upper and lower right leads 491 and 492 that extend from the right reducer drum 470 to the right thumb 18 through bores (not shown) in the right reducer housing 476. (See FIGS. 1-3 including dotted lines in FIG. 2.)

Moreover, in a manner similar to that for the left tendon 364, the right drum 470 can further be partially surrounded by an arcuate plate which assists in retaining the right thumb tendon 460 on the right reducer drum 470. (See FIG. 11.) As with the left reducer drum 374, the plate and outer surface of the right reducer drum 470 define an arcuate channel and the plate is secured to the drum by pins and a screw.

Both leads 491 and 492 pass along the exterior of the hand 10 and enter the interior of the right thumb 18 through bores (not shown) in the right thumb base 244. (See e.g. FIGS. 1 and 9.) The portion of the right tendon 460 that extends between the exterior of the right thumb 16 and the right reducer housing 476 can also be surrounded by an appropriate tubular casings 494 for preserving the useful life of the right tendon 460 (casings only partially shown in FIG. 14.)

Since the left and right thumbs 16 and 18 are of similar construction and operate similarly, it will be understood that the upper and lower leads 491 and 492 of the right thumb 18 wrap around the various right thumb pulleys and shape adaption mechanisms in the same manner as the leads 395 and 396 of left thumb 16. Thus, the upper and lower leads 491 and 492 would wrap essentially as shown in FIG. 5. The lower lead 492 is also affixed to the particular brake pulleys in the same manner as for the lower lead 396 of the left thumb 16. Additionally, as with the left thumb tendon 364, the right thumb tendon 460 is preferably made of a suitable sheathed cable. It can, however, be any tendon, wire or cord which has the requisite strength and tautness for proper pitching and retraction of the right thumb 18 and its phalanges 238, 240, and 242. Moreover, like the leads 395 and 396 of the left thumb 16, the leads 491 and 492 can also be wrapped in various other ways.

It will be appreciated that pitching or pivoting of the right thumb 18 occurs in a manner similar to that for the left thumb 16. That is, upon actuation by the right pitch motor 458, the right pitch worm 474 engages the right pitch worm gear 468, thereby causing the right reducer drum 470 to rotate about the transverse axis of the right reducer shaft 472. Since the right pitch motor 458 can rotate the right pitch shaft 464 in either a clockwise or counterclockwise direction, the right reducer drum 470 can similarly rotate either clockwise or counterclockwise. As evident from FIG. 3(a), clockwise rotation of the right reducer drum 470 would apply tension to the upper lead 491. This would cause the upper lead 491 to tend to wrap further around the right drum 470 and the lower lead 492 to tend to uncoil from it.

Consequently, the right thumb 18 would be retracted. Relative to the configuration of the right thumb 18 shown in FIG. 1, the retraction would commence at the outer right phalange 238. Conversely, when the right drum 470 rotates in a counterclockwise direction, it would apply tension to the lower lead 492. Therefore, the lower lead 492 would ten to wrap further around the drum 470 while the upper lead 491 would tend to uncoil from it. Consequently, right thumb 18 and its corresponding phalanges 238, 240 and 242 would pitch or pivot.

As set forth previously, the left and right thumbs are of similar construction. Thus, it will be appreciated that the inner and outer shape adaption mechanisms would function similar to the manner that they function in the left thumb 16 to control the sequence of pitching or pivoting of the right thumb 18.

With reference now to the engagement of the finger 14 and, particularly, to the yawing of the finger 14, the finger engagement sub-assembly 26 includes a finger yaw motor 500 and a finger yaw gear sub-assembly 502 that cooperate to cause yawing of the finger 14. As depicted in FIG. 3(b), the finger yaw motor 14 has a finger yaw shaft 504 which is rotatably connected to it and can rotate the shaft 504 in either a clockwise or counterclockwise direction. It can be any suitable dc or stepper motor, or any other motor that can provide the requisite actuation of the finger yaw shaft 504 so as to drive the finger yaw gear sub-assembly 502. The transverse axis of the finger yaw shaft 504 is oriented substantially parallel to the base axis associated with yawing of the finger 14. It is also oriented substantially perpendicular to the common transverse axis of the left primary and left common secondary shafts 300 and 302 and to the common transverse axis of the right primary and right secondary shafts 400 and 402.

The finger yaw gear sub-assembly 502 includes a primary finger yaw worm gear 506 and a finger bevel gear 508 which are each mounted on a finger primary drive shaft 510 for rotation with the finger shaft 510. The finger worm gear 506 is located toward one end of the finger shaft 510 and is engageable with a finger yaw worm 512 that is mounted for rotation with the finger yaw shaft 504. The bevel gear 508 is located at the other end of the finger shaft 510 and is engageable with a suitable finger ring gear 514 or other suitable gear that can properly engage the bevel gear 508. The transverse axis of the primary finger shaft 510 is substantially perpendicular to the finger base axis associated with yawing of the finger 14 and is substantially parallel to the common transverse axis of the left primary and left secondary drive shafts 300 and 302. (See e.g. FIGS. 1–3.) It will also be observed that the primary finger shaft 510, left primary and secondary shafts 300 and 302 and right primary and secondary shafts are all substantially located in a common shaft plane.

For the purpose of transferring the rotation of the finger bevel gear 514 into yawing of the finger 14, the finger ring gear 514 is mounted on a finger linkage shaft 516 for rotation with the linkage shaft 516. One end of the linkage shaft 516 is secured to the finger base 268 for rotation with the finger base 268. The transverse axis of the finger linkage shaft 516 is substantially parallel to the finger base axis associated with yawing of the finger 14 and substantially orthogonal to the transverse axis of the primary finger shaft 510.

Upon actuation by the finger yaw motor 500, the finger yaw shaft 504 rotates and, thereby, causes the finger yaw worm 512 to engage the finger yaw worm gear 506 which rotates the primary finger shaft 510. At the same time, the finger bevel gear 508 engages the finger ring gear 514, thereby rotating the finger linkage shaft 516. Consequently, the finger 14 yaws in a plane which substantially orthogonal to the transverse axis of the finger linkage shaft 516 and substantially parallel to the aforementioned common plane. That is, it yaws about the finger base axis associated with yawing motion. (See FIGS. 2–3(b).)

The finger yaw gear sub-assembly 502 can also have a finger yaw housing 518 which surrounds the finger bevel gear 508, ring gear 514 and finger linkage shaft 516. It further defines a side aperture for receiving the primary finger shaft 510 and a top aperture (not shown) for receiving the finger linkage shaft 516. (See FIGS. 3(b) and 13.) The top surface of the housing 518 is located adjacent to the finger base 268. Suitable upper and lower bearings 520 and 522 can be situated between the finger yaw housing 518 and the finger linkage shaft 516 in order to stabilize the shaft 516 during movement of the finger 14. A suitable nut 524 can also be affixed to the shaft 516 adjacent to the bottom of the housing 518 in order to maintain the lower bearings 522 in the housing 518. For a similar purpose, a suitable washer 526 can be disposed around the finger linkage shaft 516 and located adjacent to the upper bearings 522. Moreover, the finger linkage shaft 516 can be associated with a suitable key 530 for facilitating torque transmission between the finger ring gear 514 and the shaft 516. Thrust or other suitable bearings 532 can also be situated between the housing 518 and finger base 268.

As best depicted in FIG. 13, the primary finger shaft 510 can also be surrounded by a primary finger housing 534 and mounted within suitable bearings 536. The finger yaw shaft 504, finger yaw worm 512 and finger yaw worm gear 506 can also be surrounded by a housing 538 which is secured to the support structure 28. (See FIGS. 9 and 13.) As shown in FIG. 13, the finger yaw shaft 504 is situated within suitable bearings 540. Suitable sleeves 542 and 544 can also be disposed on opposing ends of the finger yaw shaft 504 in order to better retain the bearings 540 between the housing 538 and the shaft 504 and to strengthen the shaft 504. (See FIG. 13.) For a similar purpose, the portions of the primary finger shaft 510 located near the finger worm gear 506 can be mounted within suitable bearings 546. The bearings 546 can be retained between the housing 538 and the finger shaft 510 by suitable sleeves 548 and 550 disposed on opposing sides of the finger worm gear 506. (See FIG. 9.) Moreover, a suitable key 552 can be associated with finger shaft 510 to facilitate torque transmission between the finger shaft 510 and finger yaw worm gear 506.

For the purpose of inducing pivoting or pitching motion of the finger 14, the finger engagement sub-assembly 26 further includes a finger pitch motor 554 which actuates a finger tendon or cable 556 through driving a finger pitch gear sub-assembly 558. The finger pitch motor 554 has a finger pitch shaft 560 which is rotatably connected to it and can rotate the pitch shaft 560 in either a clockwise or counterclockwise direction. It can also be surrounded by a suitable finger pitch motor housing 562. (See e.g. FIG. 1.) The motor 554 can be any suitable dc or stepper motor or any other motor that can provide the requisite actuation of the finger pitch shaft 560 so as to drive the finger pitch sub-assembly 558. The transverse axis of the finger pitch shaft 560 is oriented substantially orthogonal to the transverse axis of the finger primary shaft 510.

The finger pitch gear sub-assembly 558 is constructed essentially similar to the left pitch gear sub-assembly 366 and has a finger pitch worm gear 564 which is substantially contiguous with a finger reducer drum 566. Both the finger pitch Worm gear 564 and finger reducer drum 566 are mounted for rotation with a finger reducer shaft 568. The finger worm gear 564 is engageable with a finger pitch worm 570 that is mounted for rotation on the finger pitch shaft 560. As such, the finger reducer shaft 568 has its transverse axis oriented substantially orthogonal to the transverse axis of the finger pitch shaft 560.

The finger pitch gear sub-assembly 558 can also be provided with additional features which enhance the stability and operational characteristics of the finger pitch sub-assembly 558. It, therefore, can be surrounded by a suitable finger reducer housing 571 which is itself secured to the support structure 28. (See FIGS. 1 and 13.) Since the finger pitch sub-assembly 558 is constructed essentially similar to the left pitch sub-assembly 366, it will be observed that it would appear as shown for the left pitch sub-assembly in FIGS. 9 and 14. Thus, for example, as shown in FIG. 13, the finger linkage shaft 516 has suitable keys 572 and is associated with suitable upper and lower bearings 574 and 576. The finger reducer drum 566 and finger pitch worm gear 564 can also be mounted better for rotation by a suitable screw 577.

The finger tendon 556 is wrapped around the finger reducer drum 566 and connected to the finger 14 in a manner that permits pivoting or pitching not only of the finger 14 at the inner or base finger joint but also of the finger phalanges 262, 264 and 266 relative to each other. More specifically, as shown in FIG. 3(b) the finger tendon 556 wraps around the finger reducer drum 566 for a plurality of revolutions in such a way that it forms upper and lower left leads 578 and 580 that extend from the drum 566 to the finger 16 through bores (not shown) in the finger reducer housing 571. (See FIGS. 1-3.)

Both leads 578 and 580 pass along the exterior of the hand 10 and enter the interior of the finger 14 through bores (not shown) in the finger base linkage 268. (See e.g. FIGS. 1 and 9.) The portion of the finger tendon 556 that extends between the exterior of the finger 14 and the finger reducer housing 571 can also be surrounded by an appropriate casing 582 for preserving the useful life of the finger tendon 556 (casing only partially shown in FIGS. 9, 13.)

As discussed previously, the particular construction of the finger engagement sub-assembly 26 that causes pitching or pivoting of the finger 14 is similar to that described for the left thumb engagement sub-assembly 22. (Compare FIGS. 3(a) and (b).) The construction of the finger 14 is similar to that of the left thumb 16. (See FIGS. 4-5.)

Thus, upon actuation by the finger pitch motor 554, the finger pitch worm 570 engages the finger worm gear 564, thereby causing the reducer drum 566 to rotate about the transverse axis of the reducer shaft 568. Since the pitch motor 554 can rotate the pitch shaft 560 in either a clockwise or counterclockwise direction, the reducer drum 566 can similarly rotate either clockwise or counterclockwise. As evident from FIG. 3(b), clockwise rotation of the reducer drum 566 would apply tension to the upper lead 578. This would cause the upper lead 578 to tend to wrap further around the drum 566 and the lower lead 580 to tend to uncoil from it. Consequently, the finger 14 would be retracted. Relative to the configuration of the finger 14 shown in FIG. 1, the retraction would commence at the outer finger phalange 262.

Conversely, when the drum 566 rotates in a counterclockwise direction, it would apply tension to the lower lead 580. Therefore, the lower lead 580 would tend to wrap further around the drum 566 while the upper lead 578 would tend to uncoil from it. Consequently, the finger and its corresponding phalanges 262, 264, and 266 would pitch or pivot. As set forth previously, the finger 14 and left thumb 16 are constructed similarly. Therefore, it will be appreciated that the inner and outer shape adaption mechanisms would function in the finger 14 as previously discussed.

From the foregoing description of the pitching of the left and right thumbs 16 and 18 and finger 14, it will be observed that the left and right thumbs can pitch toward and away from each other substantially in the aforementioned same common shaft plane. Thus, with reference to FIG. 1, the left and right thumbs 16 and 18 can roll substantially ninety degrees and then pitch in the aforementioned shaft plane. Moreover, upon rotating substantially 180 degrees from their respective rest positions shown in FIG. 2, the thumbs 16 and 18 can yaw in a plane substantially parallel to the aforementioned shaft plane. The capability of the thumbs 16 and 18 to roll at least substantially 180 degrees permits the hand to assume a wide variety of configurations. It is somewhat akin to rotating a human thumb 180 degrees through rotating a human arm a corresponding amount of degrees. Relative to their respective rest positions shown in FIG. 2, the finger 14 and thumbs 16 and 18 can also yaw together in a plane that is substantially parallel to the aforementioned common shaft plane.

The thumbs 16 and 18 and finger 14 are also advantageously, but not necessarily, sufficiently spaced apart from each other such that their respective tips can selectively converge contact each other when the thumbs 16 and 18 execute a 180 degrees or roll in combination with suitable pivoting movements of the finger 14 and thumbs 16 and 18. This provides a significant degree of sensitive "finger tip" control that is required to properly grasp and manipulate certain objects such as screw drivers and hypodermic needles.

Figure 15:
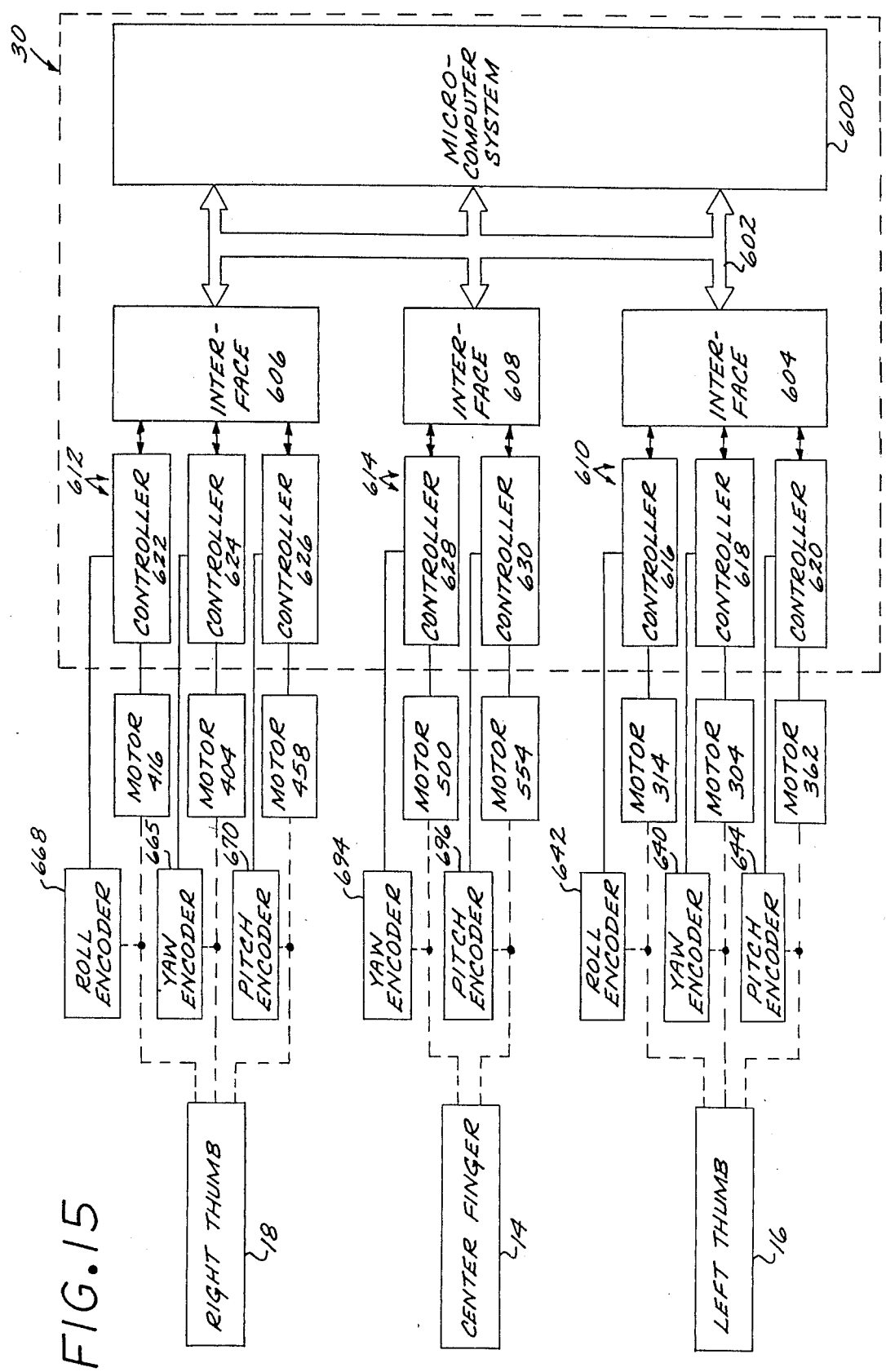
FIG. 15 is a schematic representation showing the control system of FIG. 1 and its interaction with the hand.

In accordance with still another feature of the invention, the control system 30 (see dotted lines in FIG. 15) selectively regulates the respective movements of the finger 14 and thumbs 16 and 18. As depicted in FIG. 15, the control system 30 includes a suitable microcomputer system 600, which is connected by a suitable communications bus 602 to left thumb, right thumb and finger interfaces 604, 606 and 608, that interact with suitable sets of left thumb, right thumb, and finger controllers 610, 612, and 614 respectively.

More particularly, the microcomputer system 600 formulates various commands or command signals necessary to achieve desired movements of the finger and thumbs 14, 16 and 18 and electronically transmits the commands by suitable wiring to the bus 602. The bus 602 differentiates between the commands and electronically routes or addresses each command by suitable wiring to a separate one of the interfaces 604, 606 and 608. Thus, for instance, the bus 602 would differentiate and route a command or command signal directing a specified or desired movement of the finger 14 to the finger interface 608. The bus 602 is also advantageously a two-way bus in that it can accept and assess status information from the interfaces 604, 606 and 608 on the finger 14 and thumbs 16 and 18 and communicate the status information back to the microcomputer system 600. Consequently, for example, the bus 602 can notify the microcomputer system 600 that the finger 14 has jammed or accomplished its desired movements, or moved a specified distance.

The set of left thumb controllers 610 has separate left thumb roll, yaw, and pitch or pivot controllers 616, 618, and 620. Similarly, the set of right thumb controllers 612 has separate right thumb, roll, yaw and pitch or pivot controllers 622, 624 and 626, while the set of finger controllers has separate finger yaw and pitch or pivot controllers 628 and 630. The interfaces 604, 606 and 608 electronically communicate by suitable wiring with the sets of controllers 610, 612 and 614 respectively.

That is, each interface 604, 606 and 608, interprets each command that is addressed to it by the bus 602 and directs the particular command to a separate one of the aforementioned controllers contained within the set of controllers 610, 612 and 614 to which it is linked. Thus, for instance, a particular command interpreted as directing the finger 14 to yaw would be directed by the finger interface 608 to the finger yaw controller 628. Conversely, each of the aforementioned controllers within each set of controllers 610, 612 and 614 can electronically transmit status information back to its corresponding interface 604, 606, 608 which can then be electronically transmitted to the bus 602. Thus, for example, status information that the finger 14 has completed a desired movement could be transmitted back to the interface 608 and then transmitted to the bus 602.

The left roll, yaw and pitch controllers 616, 618 and 620 electronically communicate by suitable wiring with the left roll, yaw and pitch motors 314, 304 and 362 respectively so as to regulate the rolling, yawing and pitching or pivoting of the left thumb 16. That is, each controller 616, 618 and 620 processes appropriate electrical signals from the left interface 604 and generates suitable control signals that induce an appropriate voltage for its corresponding motor 314, 304 and 362. The amount of voltage required for any one of the motors 314, 304 and 362 will substantially depend upon the dynamics of the left thumb 16, the particular movement desired for the thumb 16 and the particular task to be performed.

Similarly, the right roll, yaw and pitch controllers 622, 624 and 626 electronically communicate by suitable wiring with the right roll, yaw and pitch motors 416, 404 and 458 respectively so as to regulate the rolling, yawing and pitching or pivoting of the right thumb 18. Thus, each controller 622, 624 and 626 processes appropriate electrical signals received from the right thumb interface 606 and generates suitable control signals that induce an appropriate voltage for its corresponding motor 416, 404 and 458.

Finally, the finger yaw and pivoting or pitching controllers 628 and 630 electronically communicate with the finger yaw and finger pitch motors 500 and 554 respectively so as to regulate the yawing and pitching or pivoting of the finger 14. Therefore, each controller 628 and 630 processes appropriate electrical signals received from the finger interface 608 and generate suitable control signals that induce the appropriate electrical voltage for its corresponding motor 500 and 554.

It will be appreciated that the particular direction of yawing, rolling and pitching or pivoting will typically be a function of whether the particular controller generates a positive or negative voltage to its corresponding motor. For example, if a positive voltage were generated in the right roll motor 416 by the right roll controller 622, the right roll shaft 420 would rotate in a clockwise direction. Therefore, the right thumb 18 would rotate counterclockwise as viewed from the frame of reference of an observer sitting on the sphere 12 and looking toward the hand 10. On the other hand, if the right controller 622 were to generate a negative voltage, the right thumb 18 would roll in a counterclockwise direction. It will further be understood that various other types of control systems can be employed to regulate movements of the finger 14 and thumbs 16 and 18.

For the purpose of advantageously being able to monitor and more readily adjust the movements of the thumbs 16 and 18 and finger 14, the control system 30 can also be associated with a series of encoders. More particularly and with reference first to the left thumb 16, the left thumb engagement sub-assembly 22 can include left thumb yaw, roll and pitch or pivoting encoders 640, 642 and 644. (See FIGS. 1, 3(c) and 11.) As shown in FIG. 11, the left yaw encoder 640 has a cylindrical body 645 having a stem 646 which is received within a bore (not shown) in the left linkage shaft 312 and secured to the shaft by a suitable screw 647. It is also situated adjacent the left base linkage 40.

The left encoder 640 is further secured to the left thumb roll housing 320 by a suitable left encoder screw 648 that passes through a left yaw encoder support plate 650 which itself is secured to the side 651 of the left roll housing 320 by a suitable left plate screw 652. (See FIG. 11.) The plate 650 is substantially L-shaped and is substantially flush with the side 651 of the housing 320 and with the bottom of the body 645 of the encoder 640. It also but defines an aperture for permitting the stem 646 to pass through to the bore of the left linkage shaft 312. Consequently, the body 645 of the left yaw encoder 640 will remain substantially stationary during yawing of the thumb 16, while its stem 646 will rotate with the shaft 312. Thus, the encoder 640 will substantially detect the degree of yawing of the thumb 16 by sensing the degree of rotation or change in angular position of the left linkage shaft 312. (See FIGS. 3(c) and 11.)

As depicted in FIG. 15, the left yaw encoder 640 then generates a digit status signal indicative of the yaw movement of the left thumb 16 and electrically transmits the signal by suitable wiring back to the left yaw controller 618. The left yaw controller 618 then compares this information with the command signal from the left interface 604 relating to the desired yaw position of the left thumb 16. If this comparison reflects that the thumb 16 has not yet achieved its desired yaw position, the controller 618 then generates a control signal which adjusts the voltage in the left yaw motor 304 so that the desired yaw position can be obtained. On the other hand, if this comparison reflects that the thumb 16 has attained its desired position, the controller 618 can either shut off the motor 304 or reduce the voltage in the motor 304 to a level at which it will not actuate the thumb 16. At the same time, the controller 618 can send appropriate status information relating to the yaw movement of the thumb 16 back to the interface 604. The status information will then proceed to the microcomputer system 600 via bus 602.

The left roll encoder 642 similarly has a cylindrical body 656 having a stem (not shown) which is secured within the left roll shaft 318 of the left roll motor 314. (See FIG. 3(c).) For that purpose, the left roll shaft 318 is preferably further elongated such that it extends through the rear of the left roll motor housing 319. (See FIGS. 1 and 3(c).) As shown in FIG. 1, the left roll encoder 642 is secured to the left roll motor housing 319 by a suitable support plate 658 that is itself secured to the housing 319. The plate 658 is again substantially L-shaped and is substantially flush with the housing 319 and the top of the body 656 of encoder 642. Consequently, the body 656 of the encoder 642 will remain substantially stationary, while its stem will rotate with the left roll shaft 318. In like manner to the left yaw encoder 640, the left roll encoder 642 substantially detects the degree of rolling of the thumb 16 by sensing the degree of rotation or changes in angular position of the left roll shaft 318.

As depicted in FIG. 15, the left roll encoder 642 then generates a digit status signal indicative of the roll movement of the left thumb 16 and electronically transmits the signal by suitable wiring to the left roll controller 616. The controller 616 then compares this information with the command signal from the interface 604 relating to the desired roll position of the left thumb 16. If appropriate, it then adjusts, or reduces the voltage in the left roll motor 314 or shuts off the motor 314 in a manner similar to that of the left yaw controller 618. At the same time, the controller 616 can send information relating to the rolling of the thumb 16 back to the microcomputer system 600 in the same manner as performed by the left yaw controller 618. (See FIG. 15.)

As shown in FIG. 14, the left pitch or pivot encoder 644 has a cylindrical body 660 having a stem 662 which is secured within a bore (not shown) within the left reducer shaft 376. The body 660 of the encoder 644 is secured to the left reducer housing 380 by a suitable support plate 664. (See FIGS. 1, 3(c) and 14.) As such, the stem 662 is rotatable with the shaft 376, while the body 660 of the encoder 644 remains substantially stationary. In like manner to the left yaw encoder 640, the left pitch encoder 644 substantially detects the degree of pitching of the thumb 16 by sensing the degree of rotation or change in angular position of the left reducer shaft 376.

As depicted in FIG. 15, it then generates a digit status signal indicative of the pitching or pivoting movement of the left thumb 16 and electronically transmits the signal to the left pitch controller 620 by suitable wiring. Thereafter, the controller 620 compares this information with the command signal from the interface 604 relating to the desired pitch position of the thumb 16. If appropriate, it then adjust or reduces the voltage in the left pitch motor 362 or shuts off the motor 362 in a manner similar to that for the left yaw controller 618. At the same time, the controller 620 can send status information relating to the pitching of the left thumb 16 back to the microcomputer system 600 in a manner similar to that of the left yaw controller 618.

It will be understood that the encoders 640, 642 and 644 can be positioned in other ways as well, for example, the encoders 640 and 644 could appropriately be connected to the left yaw and pitch motor housings 307 and 370. In that event, their respective stems 646 and 662 would be secured to the left primary shaft 300 and left pitch shaft 368 respectively.

Referring next to the right thumb 18, the right thumb engagement sub-assembly 24 can include right thumb yaw, roll and pitch or pivot encoders 665, 668 and 670. (See FIGS. 2, 3(a) and 14.) As shown in FIG. 15, the right yaw encoder 665 has a cylindrical body 672 having a stem 674 which is received within a bore (not shown) in the right linkage shaft 414 and secured to the shaft 414 by a suitable screw 676. It is also situated adjacent the right thumb base or base linkage 244.

The right yaw encoder 665 is further secured to the right thumb roll housing 424 by a suitable right encoder screw 678. The screw 678 passes through a right yaw encoder support plate 680 which itself is secured to the right roll housing 424 by a suitable right plate screw 682. The plate 680 is substantially L-shaped and is substantially flush with the bottom of the body 672 of the encoder 665. It also defines an aperture for permitting the stem 674 to pass through to the bore of the right linkage shaft 414. Consequently, the body 672 of the right yaw encoder 665 will remain substantially stationary during yawing of the thumb 18, while its stem 674 will rotate with the shaft 414. Thus, the encoder 665 will substantially detect the degree of pitching of the thumb 18 by sensing the degree of rotation or change in angular position of the right linkage shaft 414. (See FIGS. 3(a) and 14.)

The right yaw, roll and pitch encoders 665, 668 and 670 are constructed and function similarly to their counterpart left, yaw, roll and pitch encoders 640, 642 and 644. (Compare, for example, FIGS. 3(a) and (c).) More particularly, as depicted in FIG. 15, the right yaw encoder 665 generates a digit status signal indicative of the movement of the right thumb 16 and electrically transmits the signal by suitable wiring back to the right yaw controller 624. The right yaw controller 624 then compares this information with the command signal from the interface 606 relating to the desired yaW position of the right thumb 18. If this comparison reflects that the thumb 18 has not yet achieved its desired yaw position, the controller 624 then generates a control signal which adjusts the voltage in the right yaw motor 404 so that the desired position can be obtained.

On the other hand, if this comparison reflects that the thumb 18 has attained its desired position, the controller 624 can either shut off the motor 404 or reduce the voltage in the motor 404 to a level at which it will not actuate the thumb 18. At the same time, the controller 624 can send appropriate status information relating to the yaw movement of the thumb 18 back to the interface 606. The status information will then proceed to the microcomputer system 600 via bus 602.

The right roll encoder 668 similarly has a cylindrical body 684 having a stem (not shown) which is secured within the right roll shaft 420 of the right roll motor 416. (See FIG. 3(a).) For that purpose, the right roll shaft 420 is preferably further elongated such that it extends through the rear of the right roll motor housing 422. (See FIG. 2 and 3(a).) As shown in FIG. 2, the right roll encoder 668 is secured to the right roll motor housing 422 by a suitable support plate 686 that is itself secured to the housing 422. The plate 686 is again substantially L-shaped and is substantially contiguous with the bottom of the body 684 of the encoder 668. Consequently, the body 684 of the encoder 668 will remain substantially stationary, while its stem will rotate with the right roll shaft 420. In like manner to the right yaw encoder 665 the right roll encoder 668 substantially detects the degree of rolling of the thumb 18 by sensing the degree of rotation or changes in position of the right roll shaft 420.

As depicted in FIG. 15, the right roll encoder 668 then generates a digit status signal indicative of the roll movement of the right thumb 18 and electronically transmits the signal by suitable wiring to the right roll controller 622. The controller 622 then compares this information with the command signal from the interface 606 relating to the desired roll position of the right thumb 18. If appropriate, it then adjusts, or reduces the voltage in the right roll motor 416 or shuts off the motor 416 in a manner similar to that of the right yaw controller 624. At the same time, the controller 622 can send information relating to the rolling of the thumb 18 back to the microcomputer system 600 in the same manner as performed by the right yaw controller 624. (See FIG. 15.)

As shown in FIG. 3(a) and partially shown in FIG. 11, the right pitch or pivot encoder 670 has a cylindrical body 688 having a stem 690 which is secured within a bore (not shown) within the right reducer shaft 472. The body 688 of the encoder 670 is secured to the right reducer housing 476 by a suitable support plate 692. (See FIG. 11.) As such, the stem 690 is rotatable with the shaft 472, while the body 688 of the encoder 670 remains substantially stationary. In like manner to the right yaw encoder 665, the right pitch encoder 670 substantially detects the degree of pitching of the thumb 18 by sensing the degree of rotation of the right reducer shaft 472.

As depicted in FIG. 15, it then generates a digit status signal indicative of the pitch or pivot movement of the right thumb 18 and electronically transmits the signal to the right pitch controller 626 by suitable wiring. Thereafter, the controller 626 compares this information with the command signal from the interface 604 relating to the desired pitch position of the thumb 18. If appropriate, it then adjust or reduces the voltage in the right pitch motor 458 or shuts off the motor 458 in a manner similar to that for the right yaw encoder 665. At the same time, the controller 626 can send status information relating to the pitching of the right thumb 18 back to the microcomputer system 600 in a manner similar to that of the right yaw controller 622.

Referring next to the finger 14, the finger engagement sub-assembly 26 can include finger yaw and pitch or pivot encoders 694 and 696. (See FIGS. 1-2, 3(b) and 13.) As shown in FIGS. 3(b) and 13, the finger yaw encoder 694 has a cylindrical body 698 having a stem 700 which is received within a bore (not shown) in the bottom of the finger linkage shaft 516 and secured to the shaft 516 by a suitable screw 702. The finger encoder 694 is further secured to the finger yaw housing 518 by a finger yaw encoder support plate 704 which itself is secured to the bottom of the finger yaw housing 518. The plate 704 is substantially L-shaped and is substantially flush with the bottom of the body 698 of the encoder 694. It also defines an aperture for permitting the stem 700 to pass through into the bore of the finger linkage shaft 516. Consequently, the body 698 of the finger yaw encoder 694 will remain substantially stationary during yawing of the finger 14, while its stem 700 will rotate with the shaft 516. Thus, the encoder 694 will substantially detect the degree of yawing of the finger 14 by sensing the degree of rotation or change in angular position of the finger linkage shaft 516. (See FIGS. 3(c) and 13.) It will be observed that, there is preferably some space clearance between the bottom of the finger linkage shaft 516 and the support plate 704. Similar spaces also preferably exist with respect to the left and right thumb yaw encoders 640 and 665. (See FIGS. 11 and 14.)

The finger yaw encoder 694 is constructed and, functions similarly to, its counterpart left yaw encoder 640, except that the finger yaw encoder 694 is oriented somewhat differently. (Compare FIGS. 3(b) and (c).) More particularly, as depicted in FIG. 15, the finger yaw encoder 694 generates a digit status signal indicative of the yaw movement of the finger 14 and electrically transmits the signal by suitable wiring to the finger yaw controller 628. The finger yaw controller 628 then compares this information with the command signal from the interface 608 relating to the desired yaw position of the finger 14. If this comparison reflects that the finger 14 has not yet achieved its desired yaw position, the controller 628 then adjusts the voltage in the finger yaw motor 500 so that the desired position can be obtained.

On the other hand, if this comparison reflects that the finger 14 has attained its desired position, the controller 628 can either shut off the motor 500 or reduce the voltage in the motor 500 to a level at which it will not actuate the finger 14. At the same time, the controller 628 can send appropriate status information relating to the yaw movement of the finger 14 back to the interface 608. The status information will then proceed to the microcomputer system 600 via bus 602.

The finger pitch or pivot encoder 696 is constructed and oriented similar to the left and right pitch encoders 644 and 670. As shown in FIG. 1, 3(b) and 13, the finger pitch encoder 696 has a cylindrical body 706 having a stem 708 which is secured within a bore (not shown) within the finger reducer shaft 568. As such, the stem 708 is rotatable with the shaft 568, while the body 706 of the encoder 696 remains substantially stationary. The body 706 of the encoder 696 is secured to the finger reducer housing 571 by a suitable support plate 710. In like manner to the left pitch encoder 644, the finger pitch encoder 696 substantially detects the degree of pitching or pivoting of the finger 14 by sensing the degree of rotation of the finger reducer shaft 568.

As depicted in FIG. 15, it then generates a digit status signal indicative of the pitch or pivot movement of the finger 14 and electronically transmits appropriate movement information to the finger pitch controller 630 by suitable wiring. Thereafter, the controller 630 compares this information with the command signal from the interface 608 relating to the desired pitch position of the finger 14. If appropriate, it then adjust or reduces the voltage in the finger pitch motor 554 or shuts off the motor 554 in a manner similar to that for the left pitch encoder 644. At the same time, the controller 630 can send status information relating to the pitching of the finger 14 back to the microcomputer system 600 in a manner similar to that of the left pitch controller 620.

It will be understood that various other forms of control systems can be fashioned in accordance with the present invention. Further, the control system 30 can of course selectively cause the finger 14 and thumbs 16 and 18 to engage in specified movements substantially in unison.

Figure 6:
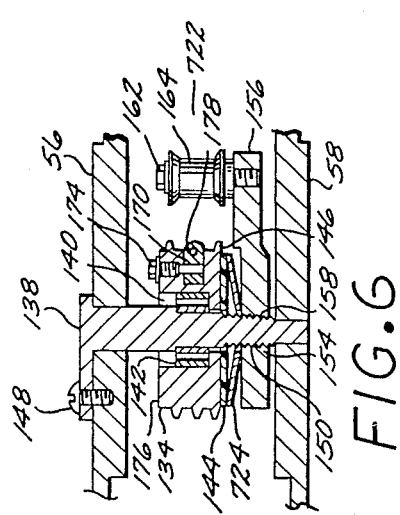
FIG. 6 is an enlarged fragmentary, transverse sectional view of an alternative embodiment of shape adaption mechanism situated within the interior of the left thumb.

An alternative embodiment of a shape adaption mechanism associated with the present invention is shown in FIG. 6. This embodiment has a shape adaption mechanism 722 and is similar in all respects to the embodiments of the inner and outer shape adaption mechanisms 130 and 132 discussed above (see FIGS. 4-5), with one exception. That is, it replaces the inner and outer friction plates 180 and 230 respective of the previous embodiment with a bellville or substantially dish-shaped washer 724 (see FIG. 6.) Consequently, it also does not, for example, have the hollow friction stem 182 or secondary brake pin 184 associated with the friction plate 180.

For simplicity, FIG. 6 depicts how the washer 724 would appear in the inner shape adaption mechanism 130 upon its supplanting the inner friction plate 230. In all other respects, however, the shape adaption mechanism 722 of this embodiment functions similarly to the inner and outer shape adaption mechanisms 130 and 132. The washer 724 has the same function as the inner and outer friction plates 180 and 230. Thus, it would move along the inner brake rod 138 upon application of sufficient force to the inner arm roller 164. Conversely, it would return to its equilibrium position when the force has sufficiently subsided. The resiliency of the washer 722 also tends to prevent it from undesirably locking with the inner brake pulley 134.

It will be understood that the above-described alternative embodiment can be situated between the various joints of the right thumb 18 and the finger 14 in the manner discussed in connection with the outer and inner shape adaption mechanisms 132 and 130 of the previous embodiment. Moreover, the particular type of biasing elements and other components chosen will again substantially depend upon the dynamics of the thumbs 16 and 18 and finger 14 and the particular tasks to be accomplished.

Figure 7:
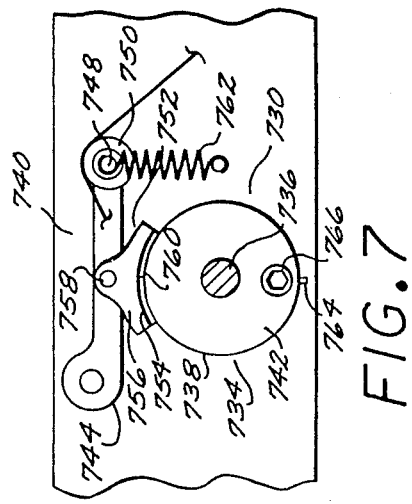
FIG. 7 is an enlarged side view of still another alternative embodiment of shape adaption mechanism.
Figure 8:
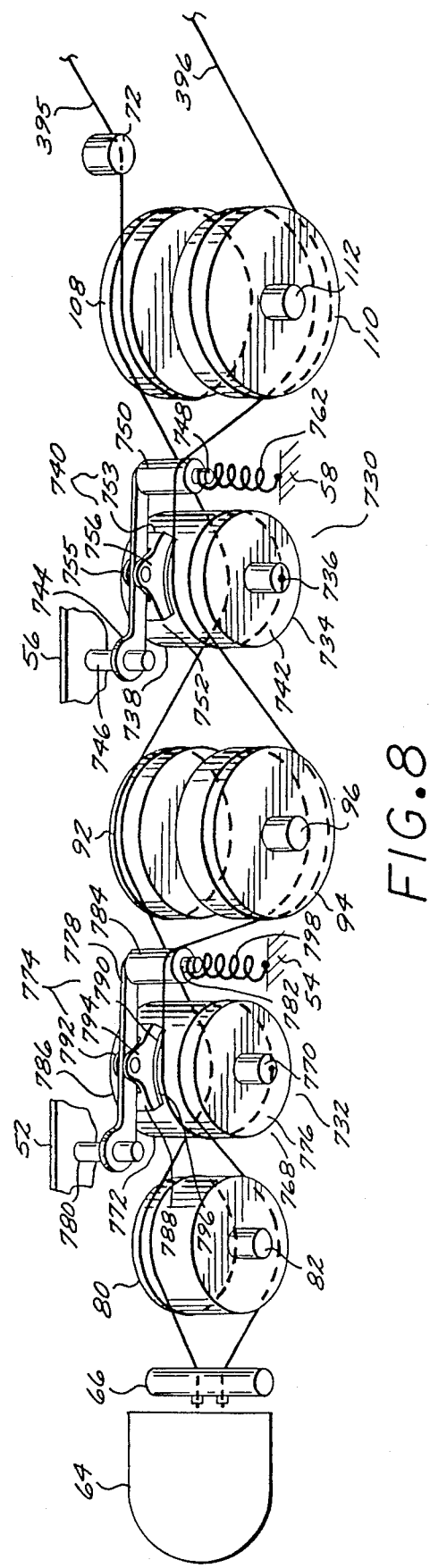
FIG. 8 is an enlarged schematic representation of the interior of the left thumb illustrating the alternative shape adaption mechanism embodiment of FIG. 7.

Still another alternative embodiment of a shape adaption mechanism associated with the present invention is shown in FIGS. 7-8. In this embodiment, inner and outer shape adaption mechanisms 730 and 732 are employed in place of the inner and outer shape adaption mechanisms 130 and 132 of the embodiment of FIGS. 4-5. The mechanisms 730 and 732, however, function essentially similar to the shape adaption mechanisms of the previously described embodiments in that they permit the same controlled sequential pitch or pivoting. More particularly, and with exemplary reference to the left thumb 16, the inner shape adaption mechanism 730 is situated between the middle and inner or base left thumb joints 76 and 78. (See FIG. 8.) It includes an inner left brake pulley 734 which is disposed around an inner left brake rod 736 and which has an outer convex surface 738 that is engageable with an inner left brake 740. (See FIGS. 7-8.)

The inner brake pulley 734 is selectively rotatable relative to the inner brake rod 736 and is constructed similarly to the inner brake rod 138 of the first embodiment. (See FIGS. 4-5 and 8.) It does not, however, have a friction pad 144 affixed to its inner radial surface 742. The inner brake rod 736 is secured to the opposing side linkages 56 and 58 of the inner left phalange 38. It is also constructed similar to the inner brake rod 138 of the first embodiment, except that it need not necessarily have external inner rod threads 150.

The inner left brake 740 includes an elongated inner brake arm 744 which is pivotally secured on one end to a secondary inner brake rod 746 and on the other end has an inner arm rod 748 connected to it. The transverse axis of the inner brake arm 744 is substantially perpendicular to the transverse axis of the inner brake rod 736. The inner brake arm 744 is also situated above the top of the outer surface 738 of inner brake pulley 734. (See FIGS. 7-8.) The secondary inner brake rod 746 is secured to the side linkage 56 of the inner left phalange 38 and has its transverse axis oriented substantially parallel to the transverse axis of the inner brake rod 736. The inner arm rod 748 has an inner arm roller 750 disposed around it. As such, the common transverse axis of the inner arm rod 748 and the inner arm roller 750 is oriented substantially parallel to the transverse axis of the inner brake rod 736.

For the purpose of applying braking force to the inner brake pulley 734, the inner brake 740 further includes an inner brake member 752 secured to the intermediate section of the inner brake arm 744. The member 752 has a substantially rectangular base 753 having a concave outer surface 754 that substantially conforms to the outer surface 738 of the inner brake pulley 734. As shown in FIGS. 7-8, the inner brake member 752 also has two opposing somewhat bell shaped sides 755 and 756 that rise from the rectangular base 753 and slant inward toward the inner brake arm 744. They are then secured to the intermediate section of the inner brake arm 744 by a suitable pin 758. The concave outer surface 754 of the inner brake member 752 can also be provided with a suitable friction pad 760. The pad 760 conforms to the concave surface 754 and the outer surface 738 and is abutable with the outer surface 738 of the inner brake pulley 734.

For the purpose of more selectively and effectively regulating the braking force exerted by the inner brake 740, the inner left brake 740 also advantageously includes a suitable biasing element 762, which can be a suitable helical spring. The biasing element 762 has one of its ends secured to the inner arm rod 748, while its other end is secured to the side linkage 58 of the inner left phalange 38.

As depicted in FIG. 8, the equilibrium or rest position of the inner brake 740 corresponds to the position in which the left thumb 16 is fully extended. In this equilibrium position, therefore, the biasing element 762 exerts a threshold initial tensile or pulling force on the inner brake arm 744. This in turn provides the inner brake member 752 with a threshold braking force that is initially exerted on the outer surface 738 of the inner brake pulley 734. However, when sufficient force becomes incident on the inner arm roller 750, the inner brake member 752 will move downward. Consequently, the braking force against the inner brake pulley 734 will augment above its threshold level and, thereby, further resist clockwise rotation of the inner brake pulley 734.

Conversely, when the force on the inner arm roller 750 has sufficiently subsided, the biasing element 762 will return the inner brake 740 to its equilibrium position. It will also be observed that the inner brake 740 can be associated with an inner tendon brake pin 764 and suitable screw pin 766 in a fashion similar to inner tendon brake pin 170 and screw pin 174 of the inner brake 136. (See FIG. 7.)

The outer shape adaption mechanism 732 is constructed essentially similar to, and functions essentially alike, the inner shaped adaption mechanism 730. More particularly, as depicted in FIG. 8, the outer shape adaption mechanism 732 is situated between the outer and middle left thumb joints 74 and 76. It includes an outer left brake pulley 768 which is disposed around an outer left brake rod 770 and which has an outer convex surface 772 which is engageable with an outer left brake 774.

The outer brake pulley 768 is selectively rotatable relative to the outer brake rod 770 and is constructed similarly to the outer brake rod 190 of the first embodiment. (See FIG. 4-5 and 8.) It does not, however, have a friction pad 196 affixed to its inner radial surface 776. The outer brake rod 770 is secured to the opposing side linkages 52 and 54 of the middle left phalange 36. It is also constructed similarly to the outer brake rod 190 of the first embodiment, except that it need not necessarily have external outer rod threads 202.

The outer left brake 774 includes an elongated outer brake arm 778 which is pivotally secured to one end of a secondary outer brake rod 780 and on the other end has an outer arm rod 782 connected to it. The transverse axis of the outer brake arm 778 is substantially perpendicular to the transverse axis of the outer brake rod 770. The outer brake arm 778 is also situated above the top of the outer surface 772 of the outer brake pulley 768. (See FIG. 8.)

The secondary outer brake rod 780 is secured to the side linkage 52 of the middle left phalange 36 and has its transverse axis oriented substantially parallel to the transverse axis of the outer brake rod 770. The outer arm rod 782 has an outer arm roller 784 preferably rotatably disposed around it. As such, the common transverse axis of the outer arm rod 782 and the outer arm roller 784 is oriented substantially parallel to the transverse axis of the outer brake rod 770.

For the purpose of applying braking force to the outer brake pulley 768, the outer brake 774 further includes an outer brake member 786. The member 786 is secured to the intermediate section of the outer brake arm 778 and is configured similar to the inner brake member 752. (See FIG. 8.) As such, it has a similar rectangular base 788 having a similar concave surface 790 and similar bell shaped sides 792 and 794. Moreover, the outer brake member 786 can also have a suitable friction pad 796. The pad 796 similarly conforms to the concave surface 790 and the outer surface 772 and is abutable with the outer surface 772 of the outer brake pulley 768.

In like manner to the inner brake 740, the outer brake 774 also advantageously includes a suitable biasing element 798, which can be a suitable helical spring. The biasing element 798 has one of its ends secured to the outer arm rod 782, while its other end is secured to the side linkage 54 of the middle left phalange 36. Thus, the biasing element 798 exerts a threshold initial force on the outer brake arm 778. This provides the outer brake member 786 with a threshold braking force that is initially exerted on the outer surface 772 of the outer brake pulley 768.

However, when sufficient force incident on the outer arm roller 784, the outer brake member 786 will move downward. Consequently, the outer brake member 786 will apply increasing braking force against the outer brake pulley 768. The outer brake pulley 768 will, therefore, be increasingly restrained from rotating clockwise relative to the outer brake rod 770. Conversely, when the force on the outer arm roller 784 has sufficiently subsided, the biasing element 798 will return the outer brake 774 to its equilibrium position. Like the inner brake 740, the outer brake 774 can also be associated with an outer tendon brake pin and a suitable screw pin for the reason previously explained.

It will be observed that the left thumb tendon 364 wraps around the inner and outer shape adaption mechanisms 730 and 732 somewhat differently than it wraps around the shape adaption mechanisms of the previous embodiments. That is, while the lower lead 396 of the left tendon 364 wraps similarly, the upper lead 395 is received by the respective undersides of the inner and outer brake pulleys 734 and 768. (See FIG. 8.) In contrast, the upper lead 395 does not contact the shape adaption mechanisms of the previous embodiments. (See FIG. 5.) It will also be appreciated that various other forms of shape adaption mechanisms that apply braking force so as to enhance the stability and control the pitching or pivoting of the left thumb, right thumb and fingers 16, 18 and 14 can be constructed in accordance with the present invention.

The inner and outer shape adaption mechanisms 730 and 732 cooperate to control the pitching or pivoting sequence of the finger 14 and left and right thumbs 16 and 18 in essentially the same manner as that described for the inner and outer shape adaption mechanisms 130 and 132 of the first embodiment. Thus, for instance, in a case similar to the first exemplary situation described above, tensile force would propagate along the lower lead 396 and cause a downward force to become incident on the inner arm roller 750. This tensile force would initially be counteracted by the threshold braking force exerted by the inner brake member 752 on the outer surface 738 of the inner brake pulley 734.

If the tensile force is sufficient to cause the inner arm roller 750 to move downward, then the inner brake member 752 will correspondingly move downward. As a result, the braking force exerted on the outer surface 738 will increase and, thereby, further restrain clockwise rotation of the inner brake pulley 734. Moreover, the increase in braking force will prevent the propagation of sufficient tensile force to accomplish pivoting or pitching of the outer, middle and inner left phalanges 34, 36 and 38 relative to each other. At the same time, the left phalanges 34, 36 and 38 as a whole will together pivot or pitch relative to the left thumb base 40, because the braking force exceeds the tensile force.

By way of further example, in a situation akin to the second situation described above, the tensile force would continue to increase until it superceded the maximum augmented braking force. The inner brake 734 would then rotate clockwise and eventually sufficient tensile force would propagate to the middle left pulley 94. This would cause the middle left phalange 36 to pivot or pitch downward relative to the inner left phalange 38. The middle left phalange 36 will then continue to pivot or pitch downward until an object obstructs its further movement.

The left pitch motor 362 would then provide increasing tensile force to the lower lead 396 so as to counteract the force exerted by the object in the area between the outer and middle left joints 74 and 76. This increasing tensile force would then propagate to the outer shape adaption mechanism 732. The mechanism 732 would then function similarly to the mechanism 730. Eventually, the increasing tensile force would supercede the maximum augmented braking force supplied by the outer brake 774. Consequently, sufficient tensile force would propagate to the outer left pulley 80. The outer left phalange 34 would then pitch or pivot relative to the middle left phalange 36 until the outer left phalange 34 contacted the object.

It will therefore again be appreciated that the above-described controlled sequential pivoting or pitching of the phalanges 34, 36 and 38 will result in the left thumb 16 versatilely and stably configuring itself so as to properly grip and, thereafter, manipulate the object. It will further be understood that the inner and outer shape adaption mechanisms 730 and 732 would function similarly for the finger 14 and right thumb 18.

Although the invention has been described in detail with reference to the presently preferred embodiments, it will be appreciated by those skilled in the art that various modifications can be made without departing from the spirit or scope of the invention. Accordingly, the scope of present invention is not to be limited by the particular embodiments above but is to be defined only by the claims set forth below and equivalents thereof.

I claim:

1. An artificial dexterous hand for conformably engaging and manipulating objects, comprising:
   an articulated digit having a digit base and first and second phalanges, said digit base being operatively interconnected to said first phalange by a base joint having a base pulley, said phalanges being operatively interconnected by a separate first phalange joint having a first phalange pulley; and
   engagement sub-assembly means for causing said phalanges to pivot relative to said base joint and for causing said second phalange to pivot relative to said first phalange, said engagement sub-assembly means including,
   a tendon received by said base pulley and by said first phalange pulley,
   actuation means for selectively tensioning said tendon, and
   first shape adaption means, responsive to and receiving said tendon, for controlling the sequence of pivoting of said phalanges through application of braking force to said tendon, said first shape adaption means being located between said base joint and said first phalange joint and being connected to said first phalange.

2. An artificial dexterous hand according to claim 1, wherein the braking force exerted by said first shape adaption means increases as said tendon is increasingly tensioned.

3. An artificial dexterous hand according to claim 1, wherein said first shape adaption means includes:
   a first brake rod connected to said first phalange and having a series of first external threads;
   a first brake pulley operatively disposed around said first brake rod and received by said tendon, and
   first braking means, engageable with said first external threads and contactable with said first brake pulley, for selectively regulating the movement of said first brake pulley through application of braking force to said first brake pulley in response to tension exerted by said tendon on said first brake pulley.

4. An artificial dexterous hand according to claim 3, wherein said first external threads define a triple-threaded screw type thread pattern.

5. An artificial dexterous hand according to claim 3, wherein said first braking means regulates the movement of said first brake pulley by applying increasing braking force as increased tension is exerted by said tendon on said brake pulley.

6. An artificial dexterous hand according to claim 3, wherein said first braking means includes:
   a first brake disc disposed around said first brake rod and engageable with said first external threads, said first brake disc having a first brake arm;
   first arm means, connected to said first brake arm, for receiving said tendon; and
   biasing means, secured to said first brake arm and to said first phalange for providing said first brake disc with a threshold braking force.

7. An artificial dexterous hand according to claim 6, wherein said first braking means further includes means, connected to said first brake pulley, for securing said tendon to said first brake pulley.

8. An artificial dexterous hand according to claim 6, wherein:
   said first braking means further includes
   a first secondary brake rod connected to said first phalange,
   a first friction plate slidably connected to said first secondary rod and disposed between said first brake disc and said first brake pulley, said first plate further being movable along said first brake rod in response to actuation from said first brake disc; and
   said first brake pulley includes a friction pad facing said first friction plate.

9. An artificial dexterous hand according to claim 6, wherein said first braking means further includes,
   a first substantially dish-shaped washer disposed around said first brake rod and located between said first brake pulley and said first brake disc, said first washer being movable along said first brake rod in response to actuation from said first brake disc.

10. An artificial dexterous hand according to claim 1, wherein said first shape adaption means includes:
    a first brake rod connected to said first phalange;
    a first brake pulley operatively disposed around said first brake rod and received by said tendon; and
    first braking means, contactable with said first brake pulley, for selectively regulating the movement of said first brake pulley through application of braking force to said first brake pulley in response to tension exerted by said tendon on said first brake pulley.

11. An artificial dexterous hand according to claim 10, wherein said first braking means regulates the movement of said first brake pulley by applying increasing braking force as increased tension is exerted by said tendon on said first brake pulley.

12. An artificial dexterous hand according to claim 10, wherein said first braking means includes:
    a secondary brake rod secured to said first phalange;
    a first brake arm having a first end and a second end, with said first end of said first brake arm being pivotally secured to said secondary brake rod near one end of said secondary brake rod;
    first arm means, connected to said first brake arm near the second end of said first brake arm, for receiving said tendon;
    a first brake member having a concave outer surface that is engageable with the outer surface of said first brake pulley, said first brake member being secured to said first brake arm; and
    a first biasing element having a first biasing end and a second biasing end, with the first biasing end of said first biasing element being secured to the second end of said first brake arm and the second biasing end of said first biasing element being secured to said first phalange.

13. An artificial dexterous hand according to claim 1, further including:

a second articulated digit having a second digit base and third and fourth phalanges, said second digit base being operatively interconnected to said third phalange by a second base joint having a second base pulley, said third and fourth phalanges being operatively interconnected by a separate second phalange joint having a second phalange pulley; and second engagement sub-assembly means for causing said third and fourth phalanges to pivot relative to said second base joint and for causing said fourth phalange to pivot relative to said third phalange, said second engagement sub-assembly means including, a second tendon received by said second base pulley and by said second phalange pulley, and second actuation means for selectively tensioning said tendon.

14. An artificial dexterous hand for conformally engaging and manipulating objects, comprising:

an articulated digit having a digit base and at least three phalanges with any successive two of said phalanges being interconnected by a separate one of a plurality of phalange joints and with one of said phalanges being interconnected to said digit base by a base joint, each of said phalange joints having a phalange pulley and said base joint having a base pulley; and engagement sub-assembly means for causing said phalanges to pivot relative to said base joint and for causing said phalanges to pivot relative to each other, said engagement sub-assembly means including, a tendon received by said base pulley and by said phalange pulleys, actuation means for selectively tensioning said tendon; and a plurality of shape adaption means, responsive to and receiving said tendon, for controlling the sequence of pivoting of said phalanges through application of braking force to said tendon, with a separate one of said shape adaption means being located between each of said joints and being connected to said digit.

15. An artificial dexterous hand according to claim 14, wherein the braking force exerted by each of said shape adaption means increases as said tendon is increasingly tensioned.

16. An artificial dexterous hand according to claim 14, wherein each of said shape adaption means includes:
a first brake rod connected to its respective phalange and having a series of first external threads;
a first brake pulley operatively disposed around said first brake rod and received by said tendon, and
first braking means, engageable with said first external threads and contactable with said first brake pulley, for selectively regulating the movement of said first brake pulley through application of braking force to said first brake pulley in response to tension exerted by said tendon on said first brake pulley.

17. An artificial dexterous hand according to claim 16, wherein said first external threads contained within each of said shape adaption means define a triple threaded screw type thread pattern.

18. An artificial dexterous hand according to claim 16, wherein said first braking means contained within each of said shape adaption means regulates the movement of said first brake pulley by applying increasing braking force as increased tension is exerted by said tendon on said first brake pulley.

19. An artificial dexterous hand according to claim 16, wherein said first braking means contained within each of said shape adaption means includes:
a first brake disc disposed around said first brake rod and engageable with said first external threads, said first brake disc having a first brake arm;
a first arm means, connected to said first brake arm, for receiving said tendon; and
biasing means, secured to said first brake arm and to its respective phalange, for providing said first disc with a threshold braking force.

20. An artificial dexterous hand according to claim 19, wherein said first braking means contained within each of said shape adaption means further includes means, connected to said first brake pulley, for securing said tendon to said first brake pulley.

21. An artificial dexterous hand according to claim 16, wherein:
said first braking means contained within each of said shape adaption means further includes
a first secondary brake rod connected to its respective phalange,
a first friction plate slidably connected to said first secondary brake rod and disposed between said first braking means and said first brake pulley, said first friction plate further being movable along said first brake rod in response to actuation from said first braking means; and
said first brake pulley includes a friction pad facing said first friction plate.

22. An artificial dexterous hand according to claim 16, wherein said first braking means contained within each of said shape adaption means further includes a first substantially dish-shaped washer disposed around said first brake rod and located between said first brake pulley and said first braking means, said first washer being movable along said first brake rod in response to actuation from said first braking means.

23. An artificial dexterous hand according to claim 14, wherein each of said shape adaption means includes:
a first brake rod connected to its respective phalange;
a first brake pulley operatively disposed around said first brake rod and received by said tendon; and
first braking means, contactable with said first brake pulley, for selectively regulating the movement of said first brake pulley through application of braking force to said first brake pulley in response to tension exerted by said tendon on said first brake pulley.

24. An artificial dexterous hand according to claim 23, wherein said first braking means contained within each of said shape adaption means regulates the movement of said first brake pulley by applying increasing braking force as increased tension is exerted by said tendon on said first brake pulley.

25. An artificial dexterous hand according to claim 23, wherein said first braking means contained within each of said shape adaption means includes:
a secondary brake rod secured to its respective phalange;
a first brake are having a first end and a second end, with said first end of said first brake arm being pivotally secured to said secondary brake rod near one end of said secondary brake rod;

first arm means, connected to said first brake arm near the second end of said first brake arm, for receiving said tendon;

a first brake member having a concave outer surface that is engageable with the outer surface of said first brake pulley, said first brake member being secured to said first brake arm; and a first biasing element having a first biasing end and a second biasing end, with the first biasing end of said first biasing element being secured to the second end of said first brake arm and the second biasing end of said first biasing element being secured to its respective phalange.

26. An artificial dexterous hand according to claim 14, further including:

a second articulated digit having a second digit base and fourth, fifth and sixth phalanges, said second digit base being operatively interconnected to said fourth phalange by a second base joint having a second base pulley, said fourth and fifth phalanges being operatively interconnected by a separate third phalange joint having a third phalange pulley and said fifth and sixth phalanges being operatively interconnected by a separate fourth phalange joint having a fourth phalange pulley; and second engagement sub-assembly means for causing said fourth, fifth and sixth phalanges to pivot relative to said second base joint and for causing said fifth phalange to pivot relative to said fourth phalange and said sixth phalange to pivot relative to said fifth phalange, said second engagement sub-assembly means including, a second tendon received by said second base pulley and by said third and fourth phalange pulleys, and second actuation means for selectively tensioning said tendon.

* * * * *

UNITED STATES PATENT AND TRADEMARK OFFICE
CERTIFICATE OF CORRECTION

PATENT NO. : 4,946,380

DATED : August 7, 1990

INVENTOR(S) : Sukhan Lee

It is certified that error appears in the above-identified patent and that said Letters Patent is hereby corrected as shown below:

On the title page:
In the abstract, line 1, "conformally" should read --conformably--.

Column 1, line 7, "Sourthern" should read --Southern--.

Column 1, line 27, "give" should read --given--.

Column 7, line 3, "of the and left thumb" should read --of the left thumb--.

Column 8, line 46, "have a inner" should read --have an inner--.

Column 8, line 68, between "shapes of objects" and "More particularly", insert --.--".

Column 10, line 51, between "the force has subsided" and "The inner", insert --.--.

Column 12, line 67, "surface 198 the of" should read --surface 198 of the--.

Column 13, line 34, "situate" should read --situated--.

UNITED STATES PATENT AND TRADEMARK OFFICE
CERTIFICATE OF CORRECTION

PATENT NO. : 4,946,380

DATED : August 7, 1990

INVENTOR(S) : Sukhan Lee

It is certified that error appears in the above-identified patent and that said Letters Patent is hereby corrected as shown below:

Column 16, line 66, between "substantially 180" and "in either", insert --degrees--.

Column 17, line 67, between "FIGS." and "and 9", insert --1--.

Column 21, line 51, between "appreciated that" and "above described", insert --the--.

Column 22, line 4, "assumed" should read --assumes--.

Column 22, line 52, "subassembly" should read --sub-assembly--.

Column 23, line 16, "Worm" should read --worm--.

Column 24, line 33, between "substantially 180" and "in either", insert --degrees--.

Column 28, line 6, "which substantially" should read --which is substantially--.

Column 29, line 7, "Worm" should read --worm--.

UNITED STATES PATENT AND TRADEMARK OFFICE
CERTIFICATE OF CORRECTION

PATENT NO. : 4,946,380

DATED : August 7, 1990

INVENTOR(S) : Sukhan Lee

It is certified that error appears in the above-identified patent and that said Letters Patent is hereby corrected as shown below:

Column 29, line 50, "Figs. 9, 13" should read --Figs. 9 and 13--.

Column 31, line 31, "604, 606, 608" should read --604, 606 and 608--.

Column 32, line 38 - 39, "It also but defines" should read --It also defines--.

Column 34, line 37, "yaW" should read --yaw--.

Column 37, line 6, between "washer 724" and "(See FIGS.", insert --.--.

Column 44, line 13, between "said first" and "disc with", insert --brake--.

Column 44, line 65, "are" should read --arm--.

Signed and Sealed this

Fifth Day of May, 1992

*Attest:*

DOUGLAS B. COMER

*Attesting Officer*  *Acting Commissioner of Patents and Trademarks*